(12) United States Patent
Gilat-Bernshtein et al.

(10) Patent No.: US 7,218,771 B2
(45) Date of Patent: May 15, 2007

(54) CAM REFERENCE FOR INSPECTION OF CONTOUR IMAGES

(75) Inventors: Tally Gilat-Bernshtein, Yavne (IL); Zeev Gutman, Kfar Mordechai (IL)

(73) Assignee: Orbotech, Ltd., Yavne (IL)

( * ) Notice: Subject to any disclaimer, the term of this patent is extended or adjusted under 35 U.S.C. 154(b) by 451 days.

(21) Appl. No.: 10/168,713

(22) PCT Filed: Dec. 22, 2000

(86) PCT No.: PCT/IL00/00855

§ 371 (c)(1),
(2), (4) Date: Jun. 24, 2002

(87) PCT Pub. No.: WO01/48465

PCT Pub. Date: Jul. 5, 2001

(65) Prior Publication Data

US 2003/0011761 A1 Jan. 16, 2003

(30) Foreign Application Priority Data

Dec. 23, 1999 (IL) ..................................... 133696

(51) Int. Cl.
*G06K 9/00* (2006.01)
(52) U.S. Cl. ................ 382/147; 356/237.4; 356/237.5; 356/394; 382/146; 382/151; 382/218; 382/286
(58) Field of Classification Search ............. 356/237.1, 356/613, 237.4, 237.5, 394; 382/145, 149, 382/151, 286, 146, 147, 218
See application file for complete search history.

(56) References Cited

U.S. PATENT DOCUMENTS

| | | | |
|---|---|---|---|
| 4,758,888 A | | 7/1988 | Lapidot |
| 4,958,374 A | | 9/1990 | Tokita et al. |
| 5,039,868 A | * | 8/1991 | Kobayashi et al. .... 250/559.08 |
| 5,392,360 A | * | 2/1995 | Weindelmayer et al. .... 382/151 |
| 5,495,535 A | | 2/1996 | Smilansky et al. |
| 5,586,058 A | | 12/1996 | Aloni et al. |
| 5,619,429 A | | 4/1997 | Aloni et al. |
| 5,680,453 A | * | 10/1997 | Akiyama et al. ............. 705/52 |
| 5,774,572 A | | 6/1998 | Caspi |

(Continued)

FOREIGN PATENT DOCUMENTS

FR 2687091 8/1993

(Continued)

OTHER PUBLICATIONS

Pujas, Ph., and Aldon, M.J., "Robust colour image segmentation," Proc. International Conference on Advanced Robotics, pp. 1-14, 1995.

(Continued)

*Primary Examiner*—Gregory Desire
(74) *Attorney, Agent, or Firm*—Sughrue Mion, PLLC

(57) ABSTRACT

This invention discloses an electrical circuit inspection system including an optical subsystem for optically inspecting an electrical circuit and providing an inspection output identifying more than two different types of regions and an analysis subsystem for analyzing the inspection output, the analyzing including comparing the inspection output with a computer file reference identifying more than two different types of regions. A method for inspecting an electrical circuit inspection is also disclosed.

57 Claims, 12 Drawing Sheets

U.S. PATENT DOCUMENTS

| | | | |
|---|---|---|---|
| 5,774,573 | A | 6/1998 | Caspi |
| 5,812,268 | A * | 9/1998 | Jackson et al. ............. 356/613 |
| 5,815,596 | A | 9/1998 | Ahuja et al. |
| 5,907,628 | A | 5/1999 | Yolles et al. |
| 5,974,169 | A | 10/1999 | Bachelder |
| 6,028,948 | A | 2/2000 | Kil et al. |
| 6,036,091 | A | 3/2000 | Spitz |
| 6,366,690 | B1 | 4/2002 | Smilansky et al. |
| 6,442,291 | B1 | 8/2002 | Whitman |
| 6,476,913 | B1 * | 11/2002 | Machida et al. ............. 356/394 |
| 6,487,307 | B1 | 11/2002 | Hennessey et al. |
| 6,519,357 | B2 * | 2/2003 | Takeuchi .................... 382/149 |
| 6,539,106 | B1 * | 3/2003 | Gallarda et al. ............. 382/149 |
| 6,577,757 | B1 | 6/2003 | DeYong et al. |
| 6,654,115 | B2 * | 11/2003 | Zemer et al. ............. 356/237.5 |
| 6,714,679 | B1 | 3/2004 | Scola et al. |
| 6,795,186 | B2 * | 9/2004 | Aspir et al. .................. 356/394 |
| 6,862,365 | B1 * | 3/2005 | Beaty et al. ................. 382/145 |
| 6,947,587 | B1 * | 9/2005 | Maeda et al. ............... 382/149 |
| 6,990,227 | B2 * | 1/2006 | Greenberg et al. .......... 382/147 |
| 7,006,212 | B2 * | 2/2006 | Savareigo et al. ....... 356/237.1 |
| 2003/0011761 | A1 * | 1/2003 | Gilat-Bernshtein et al. ...... 356/237.4 |

FOREIGN PATENT DOCUMENTS

| | | |
|---|---|---|
| FR | 2687091 A1 | 8/1993 |
| WO | WO 00/11454 | 3/2000 |
| WO | WO 00/19372 | 4/2000 |
| WO | 01/07893 A2 | 2/2001 |
| WO | 01/11565 A2 | 2/2001 |

OTHER PUBLICATIONS

Automatic watershed segmentation of randomly textured color images, Shafarenko, L.; Petrou, M.; Kittler, J.; Image Processing, IEEE Transactions on vol. 6, Issue 11, Nov. 1997 pp. 1530-1544.

D. Comaniciu and P. Meer, "Robust analysis of feature spaces: Color image segmentation," in Proc. of IEEE International Conference on Computer Vision and Pattern Recognition. 1997, pp. 750-755, IEEE CS Press.

Gonzalez, R. C. et al., Digital Image Processing, Addison Wesley, USA, Chapters 7 and 8, pp. 413-569.

Russ, J.C., The Image Processing Handbook, CRC Press, 1995, Chapters 6 and 7, USA, pp. 346-477.

Marr, D. et al., Theory of Edge Detection, Proceedings of the Royal Society of London, 1980, pp. 187-217.

Chapron, M., "A new Chronic Edge-Detector Used for Color Image Segmentation", 11th APR International Conference on Pattern Recognition, 1992, pp. 31-314., France.

Baxes, Digital Image Processing Principles and Applications, John Wiley & Sons, 1994, pp. 160-177.

Sohn et al., "Boundary Representation with Lines and Circular Arcs Using Boundary Split-and-Merge Method", IEEE 1991, pp. 707-711.

D. Lagunovsky et al. "Recognition of Integrated Circuits in Reverse Engineering", Proceedings of the 14th Int. conference on pattern recognition (1998), vol. 2, pp. 1640-1642.

Carntek AOI Reference Specification Version 2.19, Oct. 15, 1996.

Tong Fang et al., On-LINE Detection of Defects in Layered Manufacturing, IEEE Int. Conference on Robotics and Automation 1998, vol. 1, pp. 254-259.

I. Bakhadyrov et al. Defect Detection in Direct Layered Manufacturing, IEEE Int., 1998, vol. 1, pp. 4251-4256.

C. C. Jong et al. Geometrical Figure Processing for IC Layout Extracted from Silicone Die Image, Int. J. Electronics 1995, vol. 78, No. 2, pp. 367-394.

J. Pineda de Gyvez, IC Defect Sensitivity for Footprint-Type Spot Defects, IEEE Transactions on Computer Aided Design, vol. 2, No. 5, pp. 638-658.

* cited by examiner

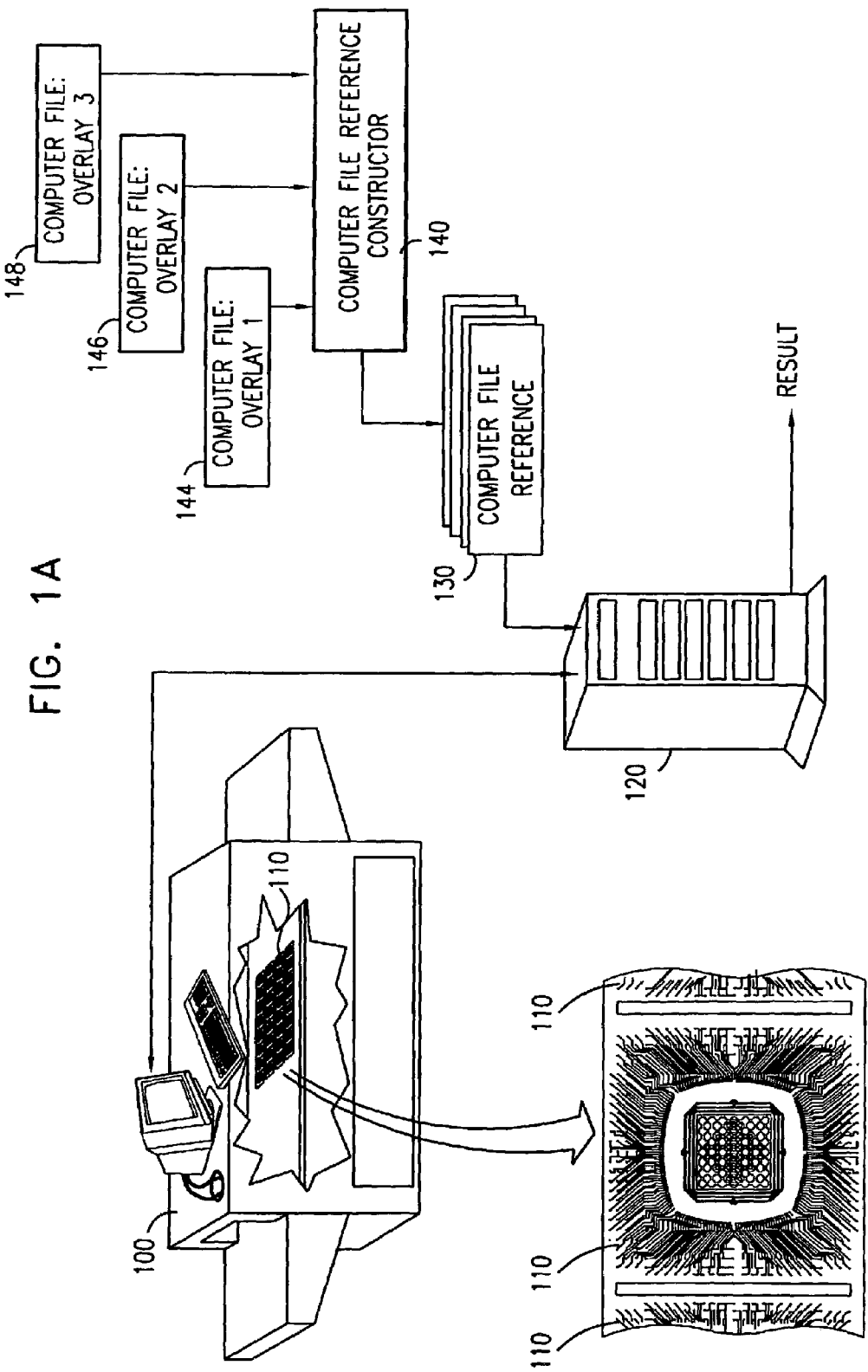

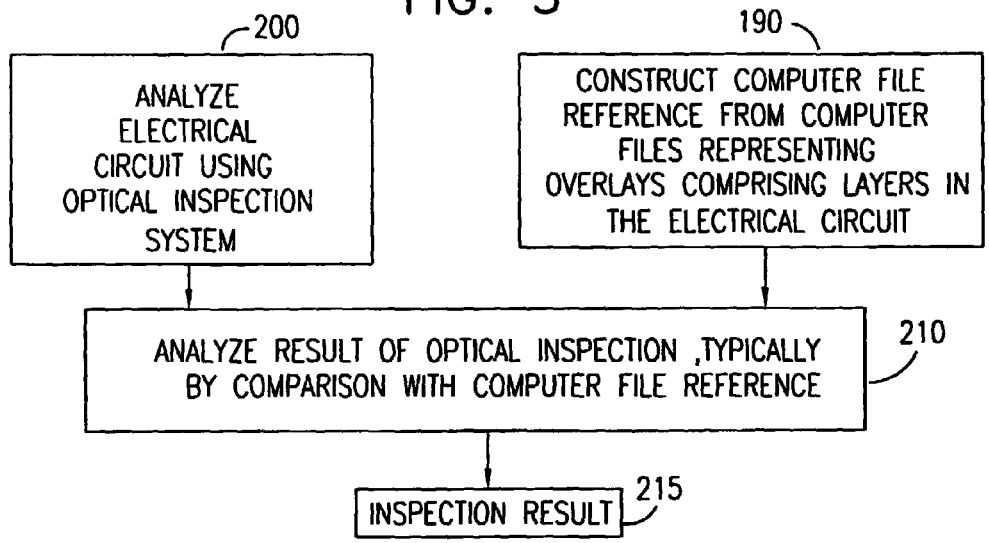
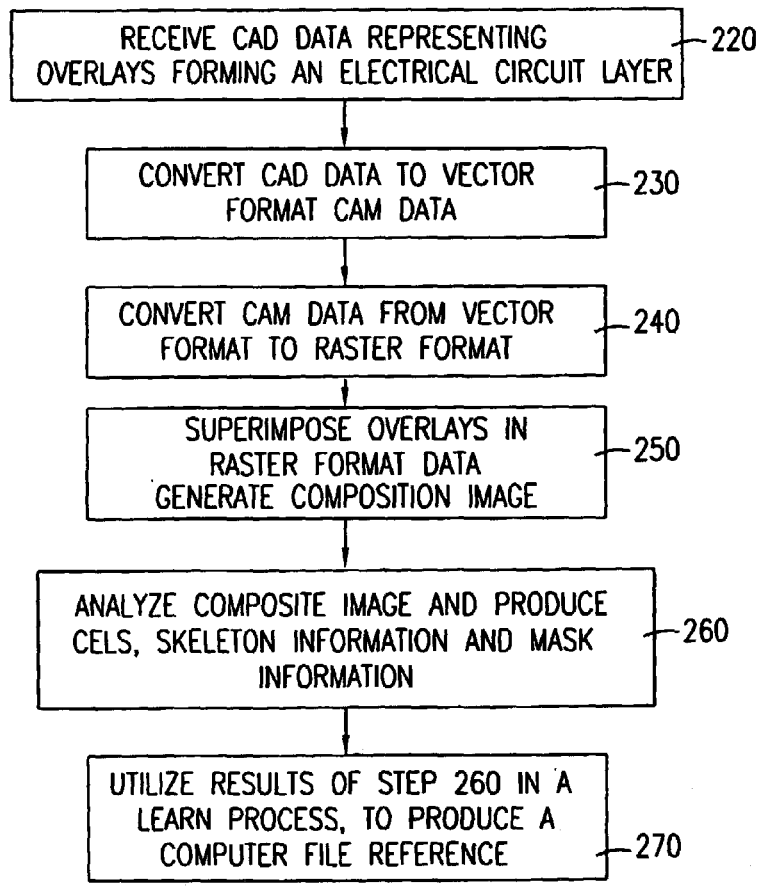

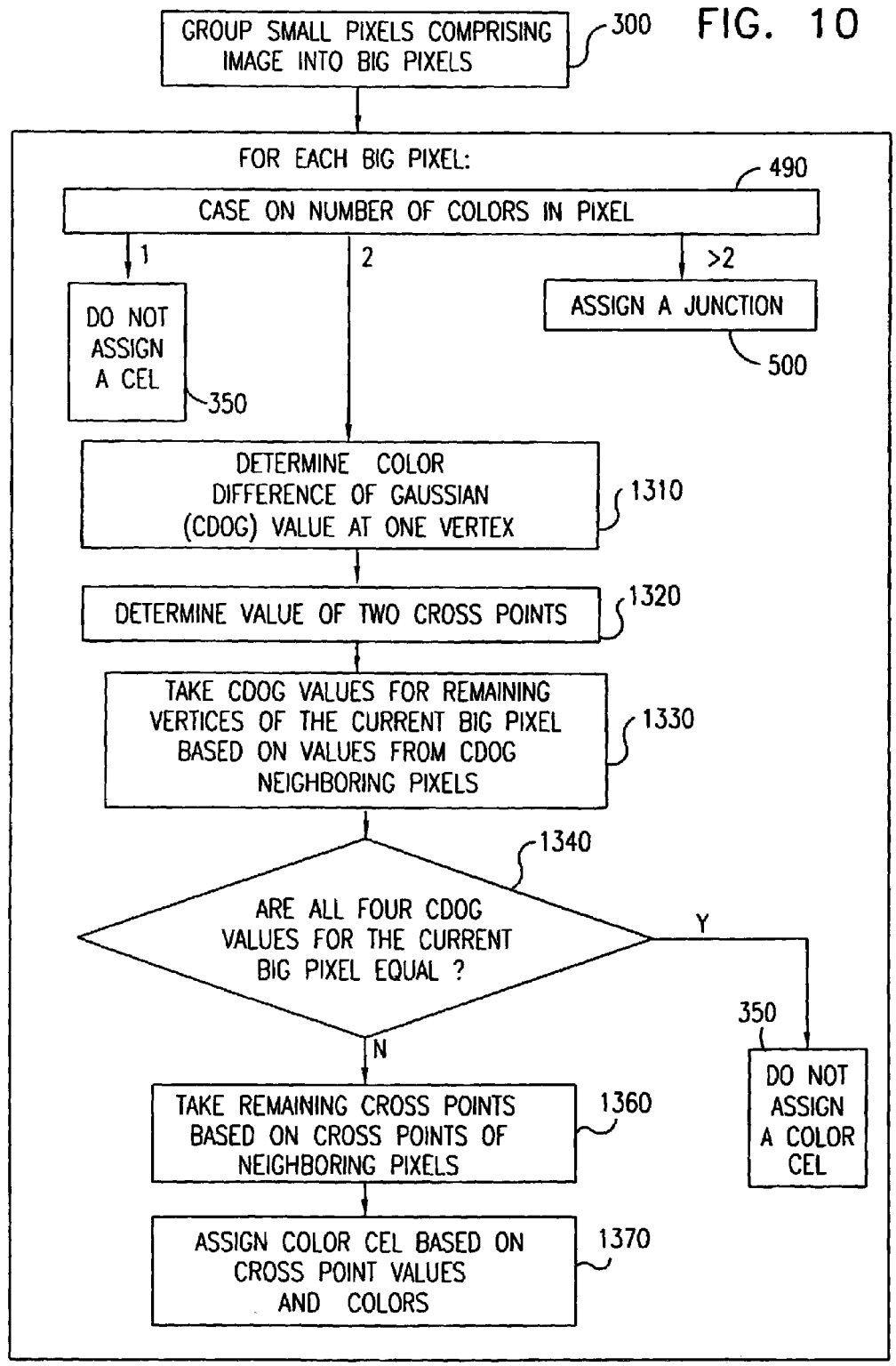

CAM REFERENCE FOR INSPECTION OF CONTOUR IMAGES

FIELD OF THE INVENTION

The present invention relates to automated optical inspection ("AOI") systems generally, and in particular to AOI systems which compare the image of a pattern under inspection, such as patterns found on electrical circuits, to a reference.

BACKGROUND OF THE INVENTION

Apparatus and methods for automatically inspecting and analyzing images of patterned articles by comparing the images to a computer generated reference, are well known in the art.

By way of example, systems that are operative to automatically optically inspect printed circuit boards by comparing images of a printed circuit board under inspection to a computer generated reference that is prepared from a computer aided manufacturing file, are generally commercially available. One typical configuration of such a system includes an Xpert 1700™ computer aided manufacturing system, CDR 300™ and Ref-Manager 300™ software appliances, and an Inspire 9000™ AOI system, all available from Orbotech Ltd. of Yavne, Israel.

Patterns inspected by conventional AOI systems typically are formed from copper conductors deposited on a non-conductive substrate. The patterns inspected are binary in nature inasmuch as only two optically identifiable populations, copper conductor and substrate, are considered.

The following co-pending patent applications, which are assigned to the same assignee as the present application and which describe apparatus and methods suitable for automatically optically inspecting patterned articles, such as electrical circuits, are hereby incorporated herein by reference:

Israel Patent Application 131092, filed Jul. 25, 1999; and

Israel Patent Application 131282, filed Aug. 5, 1999.

In co-pending Israel patent applications 131092 and 131282, hardware and software parts of an automated optical inspection system operative to inspect non-binary patterns are described. Such non-binary patterns may be found, for example, on the outer layer of a finished printed circuit board, ball grid array substrate, tape automated bonding substrate, or other similar carriers and chip packaging. These non-binary patterns, in addition to an electrical circuit, include various exotic metal coatings on selected portions of the conductors and translucent solder masks that cover selected parts of the circuit.

Conventional computer generated references of binary images, such as references typically used in the inspection of electrical circuits on printed circuit boards, do not provide complete information about the location of multiple optically identifiable populations or combinations of populations. Thus, for example, in the context of automated optical inspection of the surface of a finished ball grid array substrate, which typically includes at least copper conductors deposited on a substrate, a translucent solder mask that partly covers the conductors and gold coatings on some exposed portions of the conductors, conventional binary references used in the automated optical inspection of electrical circuits do not contain information about the existence, location and integrity of gold coatings on conductors, or about the existence, location and integrity of solder mask relative to the conductors or the substrate.

Additionally, conventional computer generated references, such as references typically used in the inspection of electrical circuits on printed circuit boards, typically provide information about pixel values for individual pixels in an image and an electrical circuit to be inspected, or about the existence and location of features in the electrical circuit. Information about the existence or location of contours and edges is not provided.

Although a reference useful for inspecting a pattern comprising multiple optically identifiable populations and/or contours and edges may be prepared from the actual inspection of a perfect or "golden" pattern, the use of a reference derived from actual inspection is problematic. As readily is appreciated, the process of preparing a reference from inspection of an article believed to have a perfect pattern is time consuming and necessitates large resources such as computer memory. Moreover, a reference prepared, for example, from a computerized design file (a "CAD file") or from a computerized manufacture file (a "CAM") file can provide information not directly available in a reference derived from actual inspection. For example, regions external to the electric circuit that do not require inspection, vias and step and repeat data may be available in a CAD file or CAM file. Additionally, there is always uncertainty as to whether the pattern used to derive a golden reference from inspection of any article was indeed perfect.

The disclosures of all references mentioned above and throughout the present specification are hereby incorporated herein by reference.

SUMMARY OF THE INVENTION

The present invention seeks to provide an improved apparatus and method for optically inspecting articles and analyzing their images, especially but not exclusively color images. The apparatus and methods of the present invention are believed to be particularly applicable to inspecting and analyzing images of a patterned article, and more particularly, applicable to analyzing images of a patterned article which includes a plurality of elements that have characteristic optical attributes.

Articles for which the apparatus and method of the present invention are particularly suited to inspect include the surfaces of ball grid array substrates ("BGA"), printed circuit board substrates, particularly printed circuit board substrates including multiple conductor materials, laminated printed circuit boards, lead frames, flat panel displays, hybrid chip packaging substrates, tape automated bonding substrates, and other similar multi-material patterned articles; for simplicity of description and without limiting the generality of the foregoing, such articles are also termed throughout the present specification and claims as "electrical circuits" and other grammatical forms thereof.

A general aspect of the present invention relates to apparatus and methods for the optical inspection of the surfaces of articles, such as electrical circuits, wherein a surface being inspected includes a non-binary pattern and is analyzed with reference to a computer file reference. The computer file reference may, for example, be constructed from a plurality of different computer files by producing a composite or superimposition of various computer files, each representing a different part of the electric circuit being inspected. The computer files may represent, for ex-ample, various deposits or overlays of materials which together comprise an electrical circuit or a single layer thereof. In the case of a single layer of an electrical circuit, the single layer typically comprises a top layer or inspectable surface suitable for being automatically optically inspected. For the sake of simplicity of description, the term "layer" is also used in the present specification and claims to include a deposit or overlay that together with additional deposits or overlays forms an inspectable surface.

Another general aspect of the present invention relates to an apparatus and method for automatically optically inspecting the surfaces of articles, such as electrical surfaces, wherein a surface of the article being inspected includes a pattern and is analyzed with reference to a computer file reference having a representation of edge contours formed by the pattern.

Still another general aspect of the present invention relates to a computer file reference which includes information relating to multiple populations, each having a different generally homogeneous optical characteristic, in a pattern on the surface of an article being inspected. The computer file reference preferably is constructed by superimposing various overlays, wherein each overlay is preferably binary in that it represents the locations at which the material is present. The optical characteristic of a pixel is determined as a function of which materials represented in the various superimposed overlays are present at a pixel.

Another general aspect of the present invention relates to a computer file reference which includes information relating to edge contour elements present in a pattern, such as a pattern on the surface of an article being inspected. Contours elements, referred to herein as CELs, may be binary or color. A binary CEL is a CEL that represents an edge between any two different populations of generally homogeneous optical characteristics. A color CEL is a CEL that represents an edge between any two different populations of generally homogeneous optical characteristics, and in addition identifies the population on either side of the edge. CELs preferably are defined to within a sub-pixel accuracy.

There is thus provided in accordance with a preferred embodiment of the present invention an electrical circuit inspection system comprising an optical subsystem for optically inspecting an electrical circuit and providing an inspection output identifying more than two different types of regions; and an analysis subsystem for analyzing said inspection output, said analyzing including comparing said inspection output with a computer file reference identifying more than two different types of regions.

Further in accordance with a preferred embodiment of the present invention the optical subsystem is capable of optically inspecting more than one layer of an electrical circuit and the two different types of regions include regions located in more than one layer of the electrical circuit.

Still further in accordance with a preferred embodiment of the present invention the two different types of regions include one or more of an exposed metal region, a metal region covered by a translucent material, an exposed substrate and a substrate covered by said translucent material.

Moreover in accordance with a preferred embodiment of the present invention the translucent material is a solder mask. Additionally and alternatively, the translucent material is a polyamide layer.

Further in accordance with a preferred embodiment of the present invention the more than two different types of regions include an exposed first metal region, a first metal region covered by a translucent material, an exposed second metal region, a second metal region covered by a translucent material, an exposed substrate and a substrate covered by said translucent material.

Still further in accordance with a preferred embodiment of the present invention the translucent material is a solder mask. Alternatively and additionally, the translucent material is a polyamide layer.

Further in accordance with a preferred embodiment of the present invention the computer file reference identifying more than two different types of regions comprises a composite of multiple computer files, each representing a different layer of said electrical circuit.

Alternatively in accordance with a preferred embodiment of the present invention the computer file reference identifying more than two different types of regions comprises an overlay of multiple computer files, each representing a different layer of said electrical circuit.

Alternatively, in accordance with a preferred embodiment of the present invention the computer file reference identifying more than two different types of regions comprises multiple computer files, each representing a different layer of said electrical circuit, superimposed in mutual registration.

Further in accordance with a preferred embodiment of the present invention the said computer file reference comprises a computer file of at least one metal layer and at least one layer of a translucent material overlying said at least one metal layer, superimposed in mutual registration.

Still further in accordance with a preferred embodiment of the present invention the computer file reference is a polychromatic reference.

Moreover in accordance with a preferred embodiment of the present invention the inspection output is a polychromatic output.

Additionally in accordance with a preferred embodiment of the present invention the computer file reference comprises at least one CAM file.

There is thus provided in accordance with a preferred embodiment of the present invention apparatus for constructing a computer file reference identifying more than two different types of regions on an electrical circuit, the apparatus comprising a superimposer for superimposing in mutual registration at least two computer files, each representing a different portion of said electrical circuit.

Further in accordance with a preferred embodiment of the present invention the different types of regions are optically distinguishable.

Still further in accordance with a preferred embodiment of the present invention the portion is a layer of the electrical circuit, and a plurality of layers form an inspectable surface of the electrical circuit.

Moreover, in accordance with a preferred embodiment of the present invention the more than two different types of regions include an exposed metal region, a metal region covered by a translucent material, an exposed substrate and a substrate covered by said translucent material.

Additionally, in accordance with a preferred embodiment of the present invention the translucent material is a solder mask. Alternatively, the translucent material is a polyamide layer.

Further in accordance with a preferred embodiment of the present invention the more than two different types of regions include an exposed first metal region, a first metal region covered by a translucent material, an exposed second metal region, a second metal region covered by a translucent material, an exposed substrate and a substrate covered by said translucent material.

Additionally in accordance with a preferred embodiment of the present invention the translucent material is a solder mask. Alternatively the translucent material is a polyamide layer.

Still further in accordance with a preferred embodiment of the present invention the computer file reference identifying more than two different types of regions comprises a composite of multiple computer files, each representing a different layer of said electrical circuit.

Moreover in accordance with a preferred embodiment of the present invention the said computer file reference identifying more than two different types of regions comprises an overlay of multiple computer files, each representing a different layer of said electrical circuit.

Alternatively in accordance with a preferred embodiment of the present invention the said computer file reference identifying more than two different types of regions comprises multiple computer files, each representing a different layer of said electrical circuit, superimposed in mutual registration.

Further alternatively in accordance with a preferred embodiment of the present invention the said computer file reference comprises a computer file of at least one metal layer and at least one layer of a translucent material overlying said at least one metal layer, superimposed in mutual registration.

Still further in accordance with a preferred embodiment of the present invention the said computer file reference comprises at least one CAM file.

There is thus provided in accordance with a another preferred embodiment of the present invention a computer file reference useful in an electrical circuit inspection system comprising at least one computer originated computer file representing more than two different types of regions in said electrical circuit Further in accordance with a preferred embodiment of the present invention regions are optically distinguishable.

Still further in accordance with a preferred embodiment of the present invention the at least one computer originated computer file represents more than two different types of regions in said electrical circuit, wherein each region is one of: a material forming part of an electrical circuit, a composite of at least two materials forming part of an electrical circuit.

Alternatively in accordance with a preferred embodiment of the present invention the at least one computer file comprises a combination of multiple computer files, each file representing a different layer of an electrical circuit, and wherein the reference identifies more than two different types of regions.

Further in accordance with a preferred embodiment of the present invention the at least one computer file is derived from multiple computer files, each computer file representing a different layer of an electrical circuit, wherein the reference identifies more than two different types of regions.

Still further in accordance with a preferred embodiment of the present invention the reference comprises an overlay of multiple computer files, each overlay representing a different layer of said electrical circuit.

Moreover in accordance with a preferred embodiment of the present invention the computer file reference which identifies more than two different types of regions comprises multiple computer files, wherein each represents a different layer of said electrical circuit, and the computer files superimposed in mutual registration.

Additionally, in accordance with a preferred embodiment of the present invention the computer file reference includes a computer file of at least one metal layer and at least one layer of a translucent material overlying said at least one metal layer, superimposed in mutual registration.

Further in accordance with a preferred embodiment of the present invention the computer file reference is a polychromatic reference.

Still further in accordance with a preferred embodiment of the present invention the inspection output is a polychromatic output.

There is thus provided in accordance with a preferred embodiment of the present invention a method for determining a contour element (CEL) in each of a plurality of big pixels forming an image, each big pixel comprising an array of small pixels, the method comprising:
  assigning an array of small pixels to each big pixel;
  performing the following steps for each big pixel:
    computing a difference of gradients sign (referred to as a DOG sign) at one vertex of the big pixel;
    determining two cross points along two edges of the big pixel, each cross point representing a value crossover between pixels having a first value and pixels having a second value;
    determining DOG signs for remaining vertices of the big pixel based on DOG values assigned to neighboring pixels of the big pixel; and
    if at least one DOG sign at one vertex of the big pixel differs from at least one DOG sign at one other vertex of the big pixel:
      determining remaining cross points along remaining edges of the big pixel; and
      assigning a CEL based on a result of the determining remaining cross points step.

There is thus provided in accordance with a preferred embodiment of the present invention a method for determining a color contour element (CEL) in each of a plurality of big pixels forming an image, each big pixel comprising an array of small pixels, the method comprising:
  assigning an array of small pixels to each big pixel;
  performing the following steps for each big pixel:
  determining a number of colors of small pixels comprised in the big pixel;
  if the number of colors is equal to one, concluding the method;
  if the number of colors is greater than two, indicating that a junction exists in the big pixel and terminating the method;
  otherwise, the number of colors being two, performing the following steps:
    computing a difference of gradients sign (DOG sign) at one vertex of the big pixel;
    determining two cross points along two edges of the big pixel, each cross point representing a value crossover between pixels having a first value and pixels having a second value;
    determining DOG signs for remaining vertices of the big pixel based on DOG values assigned to neighboring pixels of the big pixel; and
    if at least one DOG sign at one vertex of the big pixel differs from at least one DOG sign at one other vertex of the big pixel:
      determining remaining cross points along remaining edges of the big pixel; and
      assigning a color CEL based on a result of the determining remaining cross points step and on the colors of small pixels comprised in the big pixel.

Further in accordance with a preferred embodiment of the present invention each color CEL defines an edge between two populations of homogeneous optical characteristics, and identifies the population on either side of the color CEL.

There is thus provided in accordance with a preferred embodiment of the present invention an electrical circuit inspection method comprising optically inspecting an electrical circuit and providing an inspection output identifying more than two different types of regions; and analyzing said inspection output, said analyzing including comparing said inspection output with a computer file reference identifying more than two different types of regions.

Further in accordance with a preferred embodiment of the present invention the method includes superimposing in mutual registration at least two computer files, each representing a different layer of said electrical circuit.

There is thus provided in accordance with a preferred embodiment of the present invention apparatus for determining a contour element (CEL) in each of a plurality of big pixels in an image, each big pixel comprising an array of small pixels, the apparatus comprising:

a pixel assigner operative to assign an array of small pixels to each big pixel;

a CEL determiner operative, for each big pixel:
to compute a difference of gradients sign (DOG sign) at one vertex of the big pixel;
to determine two cross points along two edges of the big pixel, each cross point representing a value crossover between pixels having a first value and pixels having a second value;
to determine DOG signs for remaining vertices of the big pixel based on DOG values assigned to neighboring pixels of the big pixel; and
if at least one DOG sign at one vertex of the big pixel differs from at least one DOG sign at one other vertex of the big pixel:
to determine remaining cross points along remaining edges of the big pixel; and
to assign a CEL based on a result of the determining remaining cross points step.

There is thus provided in accordance with a preferred embodiment of the present invention apparatus for determining a color contour element (color CEL) in each of a plurality of big pixels in an image, each big pixel comprising an array of small pixels, the apparatus comprising:

and assigner operative to assign an array of small pixels to each big pixel;

a color cel determiner operative, for each big pixel:
to determine a number of colors of small pixels comprised in the big pixel;
if the number of colors is equal to one, to conclude the method;
if the number of colors is greater than two, to indicate that a junction exists in the big pixel and terminating the method;
otherwise, the number of colors being two:
to compute a difference of gradients sign (DOG sign) at one vertex of the big pixel;
to determine two cross points along two edges of the big pixel, each cross point representing a value crossover between pixels having a first value and pixels having a second value;
to determine DOG signs for remaining vertices of the big pixel based on DOG values assigned to neighboring pixels of the big pixel; and
if at least one DOG sign at one vertex of the big pixel differs from at least one DOG sign at one other vertex of the big pixel:
to determine remaining cross points along remaining edges of the big pixel; and
to assign a color cel based on a result of the determining remaining cross points step and on the colors of small pixels comprised in the big pixel.

There is thus provided in accordance with a preferred embodiment of the present invention an electrical circuit inspection system including an optical subsystem for optically inspecting an electrical circuit and providing an inspection output identifying edges between at least two different regions in the electrical circuit; and an analysis subsystem for analyzing said inspection output, said analyzing including comparing said inspection output with a computer file reference identifying edges between at least two different regions.

Further in accordance with a preferred embodiment of the present invention the optical subsystem is capable of optically inspecting more than one layer of an electrical circuit and said more than two different regions include regions at more than one layer of said electrical circuit.

Still further in accordance with a preferred embodiment of the present invention the more than two different regions include two or more of an exposed metal region, a metal region covered by a translucent material, an exposed substrate and a substrate covered by said translucent material.

Still further in accordance with a preferred embodiment of the present invention the translucent material is a solder mask. Alternatively translucent material is a polyamide layer.

Moreover in accordance with a preferred embodiment of the present invention the more than two different regions include an exposed first metal region, a first metal region covered by a translucent material, an exposed second metal region, a second metal region covered by a translucent material, an exposed substrate and a substrate covered by said translucent material.

Further in accordance with a preferred embodiment of the present invention the translucent material is a solder mask. Alternatively, the translucent material is a polyamide layer.

Still further in accordance with a preferred embodiment of the present invention the computer file reference identifying more than two different regions, includes a composite of multiple computer files, each representing a different layer of the electrical circuit.

Additionally or alternatively the computer file reference identifying more than two different regions comprises an overlay of multiple computer files, each representing a different layer of said electrical circuit.

Preferably the computer file reference identifying more than two different regions, includes multiple computer files, each representing a different layer of the electrical circuit, superimposed in mutual registration.

Still further in accordance with a preferred embodiment of the present invention the computer file reference includes a computer file of at least one metal layer and at least one layer of a translucent material overlying the metal layer, superimposed in mutual registration.

Further in accordance with a preferred embodiment of the present invention the computer file reference is a polychromatic reference.

Additionally in accordance with a preferred embodiment of the present invention the inspection output is a polychromatic output.

Still further in accordance with a preferred embodiment of the present invention the computer file reference includes at least one CAM file. Additionally or alternatively the computer file reference includes a plurality of CAM files.

There is also provided in accordance with yet another preferred embodiment of the present invention a method for electrical circuit inspection. The method includes optically inspecting an electrical circuit and providing an inspection output identifying edges between at least two different regions in the electrical circuit and analyzing the inspection output. The analysis includes comparing the inspection output with a computer file reference identifying edges between at least two different regions.

Further in accordance with a preferred embodiment of the present invention the optical inspection includes optically inspecting more than one layer of an electrical circuit and the more than two different regions, including regions at more than one layer of the electrical circuit.

Still further in accordance with a preferred embodiment of the present invention the more than two different regions include an exposed metal region, a metal region covered by a translucent material, an exposed substrate and a substrate covered by the translucent material.

Additionally in accordance with a preferred embodiment of the present invention the translucent material is a solder mask. Alternatively the translucent material is a polyamide layer.

Further in accordance with a preferred embodiment of the present invention the more than two different regions include an exposed first metal region, a first metal region covered by a translucent material, an exposed second metal region, a second metal region covered by a translucent material, an exposed substrate and a substrate covered by the translucent material.

Still further in accordance with a preferred embodiment of the present invention the computer file reference identifying more than two different regions includes a composite of multiple computer files, each representing a different layer of the electrical circuit.

Moreover in accordance with a preferred embodiment of the present invention the computer file reference identifying more than two different regions includes an overlay of multiple computer files, each representing a different layer of the electrical circuit.

Further in accordance with a preferred embodiment of the present invention the computer file reference identifying more than two different regions includes multiple computer files, each representing a different layer of said electrical circuit, superimposed in mutual registration.

Still further in accordance with a preferred embodiment of the present invention the computer file reference includes a computer file of at least one metal layer and at least one layer of a translucent material overlying the at least one metal layer, superimposed in mutual registration.

Additionally in accordance with a preferred embodiment of the present invention the computer file reference is a polychromatic reference. Alternatively, the inspection output is a polychromatic output.

Further in accordance with a preferred embodiment of the present invention the computer file reference includes at least one CAM file. Additionally or alternatively the computer file reference includes a plurality of CAM files.

BRIEF DESCRIPTION OF THE DRAWINGS

The present invention will be understood and appreciated more fully from the following detailed description, taken in conjunction with the drawings in which:

FIG. 1A is a simplified block diagram illustration of an electrical circuit inspection system constructed and operative in accordance with a preferred embodiment of the present invention;

FIG. 3 is a simplified flow chart illustrating a preferred method of operation of the system of FIG. 1;

FIG. 4 is a simplified flow chart illustrating operation of part of the system of FIG. 1, shown in FIG. 2, which relates to generation of a computer file reference;

FIG. 10 is a simplified flowchart illustration of a preferred method of operation of a portion of the apparatus of FIG. 2, which relates to color CEL generation.

DETAILED DESCRIPTION OF A PREFERRED EMBODIMENT

Reference is now made to FIG. 1A which is a simplified block diagram illustration of an electrical circuit inspection system constructed and operative in accordance with a preferred embodiment of the present invention. The system of FIG. 1A preferably includes an optical inspection subsystem 100, suitable for the inspection of articles such as electrical circuits. The optical inspection subsystem 100 preferably is operative to provide an inspection output identifying more than two different types of regions in an inspected electrical circuit. Additionally, optical inspection subsystem 100 preferably is operative to provide an inspection output identifying edges, or contours, between at least two different types of regions in an inspected electrical circuit.

The term "types of regions", as used throughout the present specification and claims, may refer, for example, to any of the following or similar types of regions:

1. A plurality of regions of different color characteristics.
2. A plurality of regions of different material or of different layers of material generally.
3. A plurality of regions including, for example, an exposed metal region, an exposed metal region coated by an exotic metal, a metal region covered by a translucent material, an exposed substrate region and a substrate region covered by a translucent material; the translucent material may be, for example, a polyamide layer or solder mask.

Figure 1B:
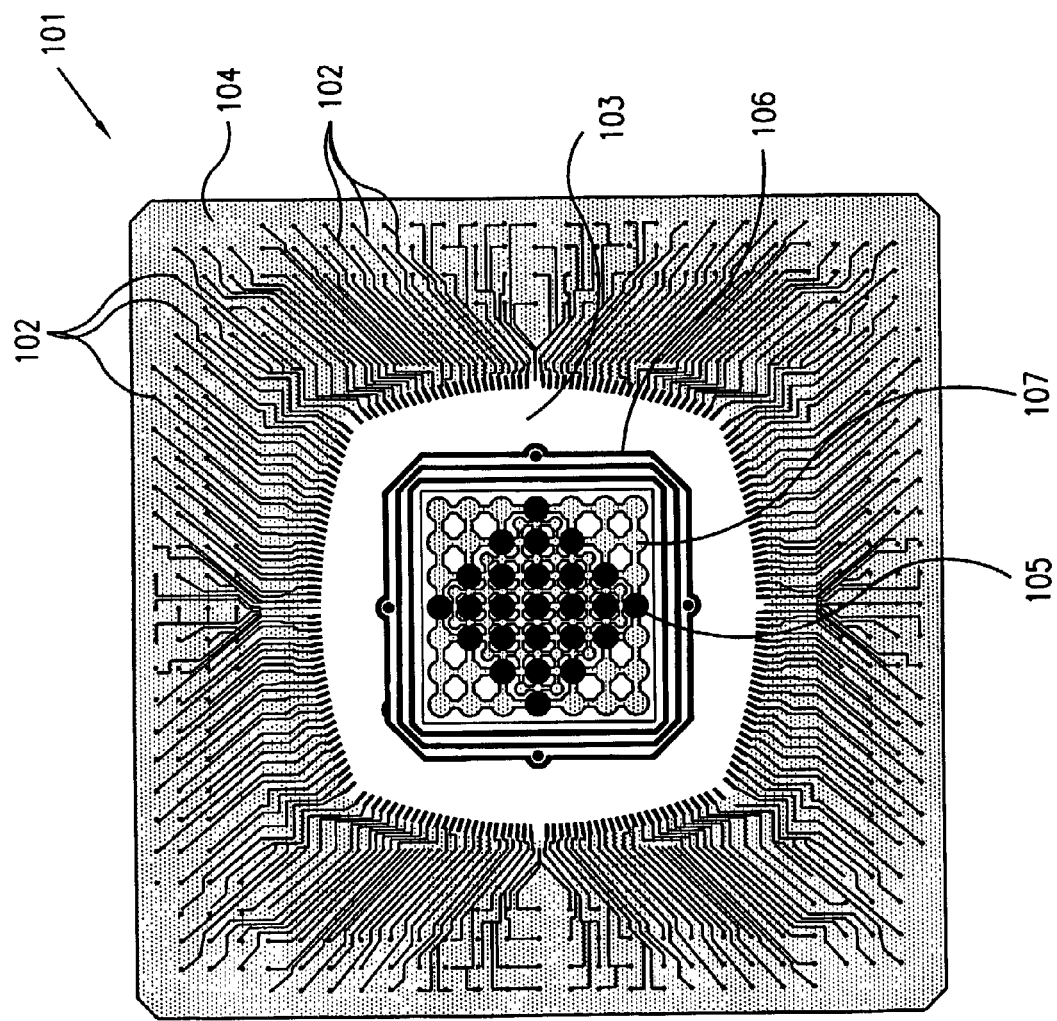
FIG. 1B is a simplified pictorial illustration of an electrical circuit, useful in understanding the present invention.

Reference is now additionally made to FIG. 1B, which is a simplified pictorial illustration of an electrical circuit, useful in understanding the present invention. The following description of FIG. 1B will assist in understanding the term "types of regions" as described above.

The apparatus of FIG. 1B is intended to provide a particular example of an article which may be optically inspected and analyzed using the present invention. The example of FIG. 1B is not meant to be limiting.

The apparatus of FIG. 1B comprises an electrical circuit 101, comprising in the example of FIG. 1B a ball grid array (BGA) substrate. The BGA 101, as is well known in the art, typically comprises: regions of copper conductor which are covered by a partially transparent or translucent coating such as a solder mask 102, regions of bare substrate 103, regions of substrate covered by partially transparent or translucent solder mask 104, regions of copper conductor coated with a metal plating such as gold, for example balls 105 and power lines 106. Additionally, some of the regions plated with gold may also be covered by partially transparent or translucent solder mask, such as covered balls 107.

It is appreciated that each of the regions of different materials and combinations of materials described hereinabove are characterized by a distinguishable color population. For example, regions of bare copper and gold plated copper are distinguishable by color. Solder-mask typically is green, and copper covered by solder mask typically is a shade of light green, gold plated copper covered by solder mask typically is a shade of very light green, and substrate covered by solder mask typically is a shade of dark green. It is appreciated that solder mask and other materials and combinations of materials present on an electrical circuit may be other colors.

As described in co-pending Israel Patent Application 131092, filed Jul. 25, 1999, which has been incorporated herein by reference, each of the different color populations associated with a material or combination of materials can be identified, and one or more of the following representations may be produced to represent a region of uniform color population: binary contour elements (contour elements are referred to herein as "CELs"), representing a boundary or edge between any two color populations; color CELs, representing a boundary or edge between any two color populations and identifying the respective color populations therealong; morphology features, representing the skeleton shape of a color population; and color morphology features representing the skeleton shape of a color population and identifying the respective color population.

It is appreciated that a wide variety of suitable image processing and analysis systems may be used as the optical inspection subsystem 100. The software and hardware parts of one particular example of a suitable image processing and analysis system is described in the following co-pending applications which are assigned to the assignee of the present application, the disclosures of which have been incorporated herein by reference:

Israel Patent Application 131092, filed Jul. 25, 1999; and
Israel Patent Application 131282, filed Aug. 5, 1999.

Referring back to FIG. 1A, the optical inspection subsystem 100 receives for inspection an electrical circuit 110, such as the BGA 101 shown in FIG. 1B. Although, electrical circuit 110 is depicted in FIG. 1A, by way of example only, as a BGA, it is appreciated that any suitable electrical circuit, or other suitable patterned article, may be inspected.

The system of FIG. 1A also preferably includes an analysis subsystem 120, typically implemented in a suitable combination of software and general-purpose hardware. The analysis subsystem 120 may also include, at least in part, special purpose hardware for optimum performance.

The analysis subsystem 120 preferably receives the inspection output for the electrical circuit 110 being inspected from the optical inspection subsystem 100, designated an "online" inspection output, and preferably is operative to analyze the online inspection output with reference to a computer file reference 130. The computer file reference 130 preferably identifies more than two different types of regions, such as more than two regions of uniform color population, and edge contours between the various regions, as described above. Thus, the analysis subsystem 120 preferably is operative to analyze the online inspection output, at least in part by comparing and analyzing the inspection output, which preferably identifies CELs, features and more than two different types of regions, with the computer file reference 130, which also preferably identifies CELs, features and more than two different types of regions, and to produce a result of the analysis.

Preferably, the result produced by the analysis subsystem 120 includes an indication of differences between the inputs to the analysis subsystem 120. In a preferred implementation of the present invention, the computer file reference 130 is representative of an ideal form of the electrical circuit 110, and the result produced by the analysis subsystem 120 represents deviations or errors in the online inspection output for electrical circuit 110 as compared to the ideal representation.

The computer file reference 130 preferably comprises a computer originated computer file. The term "computer originated computer file" is used herein to refer to a computer file such as a computer-aided manufacturing (CAM) file, a computer-aided design (CAD) file, and any other appropriate type of computer file which may originate in a computer and in interaction between a computer and a user thereof. The term "computer originated computer file" is intended to exclude a reference file derived from inspection of an article believed to be a not defective or a "golden" article, such as a computer file derived from an optical inspection system of the type described above with reference to the optical inspection subsystem 100.

Preferably, at least a portion of the computer file reference 130 has a format similar to that of at least a portion of the inspection output of the optical inspection subsystem 100, thus allowing the analysis subsystem 120 to operate more efficiently, in performing an analysis as described above, for example by comparing similar data. Alternatively, it is appreciated that the analysis subsystem 120 may be operative to convert one or both of the computer file reference 130 and the inspection output of the optical inspection subsystem 100 into a similar or common format. Further alternatively, a compatible conversion unit (not shown) may be provided separately to perform the conversion.

It is appreciated that the analysis subsystem 120 preferably is operative to register the computer file reference and the online inspection outputs. Methods for dynamically registering online inspection outputs to a reference are well known in the art. A preferred method for dynamically registering online inspection outputs and a computer file reference is described in U.S. Pat. No. 5,495,535 to Harel et al., the disclosure of which is incorporated here by reference.

The computer file reference 130 preferably is produced by a computer file reference constructor 140. The computer file reference constructor 140 preferably is operative to produce the computer file reference 130 from a plurality of inputs. The plurality of inputs to the computer file reference constructor 140 preferably comprises a plurality of files, such as CAM files, each describing one overlay corresponding to part of a design of a layer of the electrical circuit 110. The layer may be, for example, a single layer, such as the outer layer of a multi-layered circuit. First, second and third computer files 144, 146, and 148, representing respectively first, second, and third overlays, are shown by way of example only. The computer file reference constructor 140 may produce the computer file reference 130 using any appropriate method, such as by producing a composite or superimposition, particularly a superimposition in mutual registration, of the computer files 144, 146, and 148.

Figure 2:
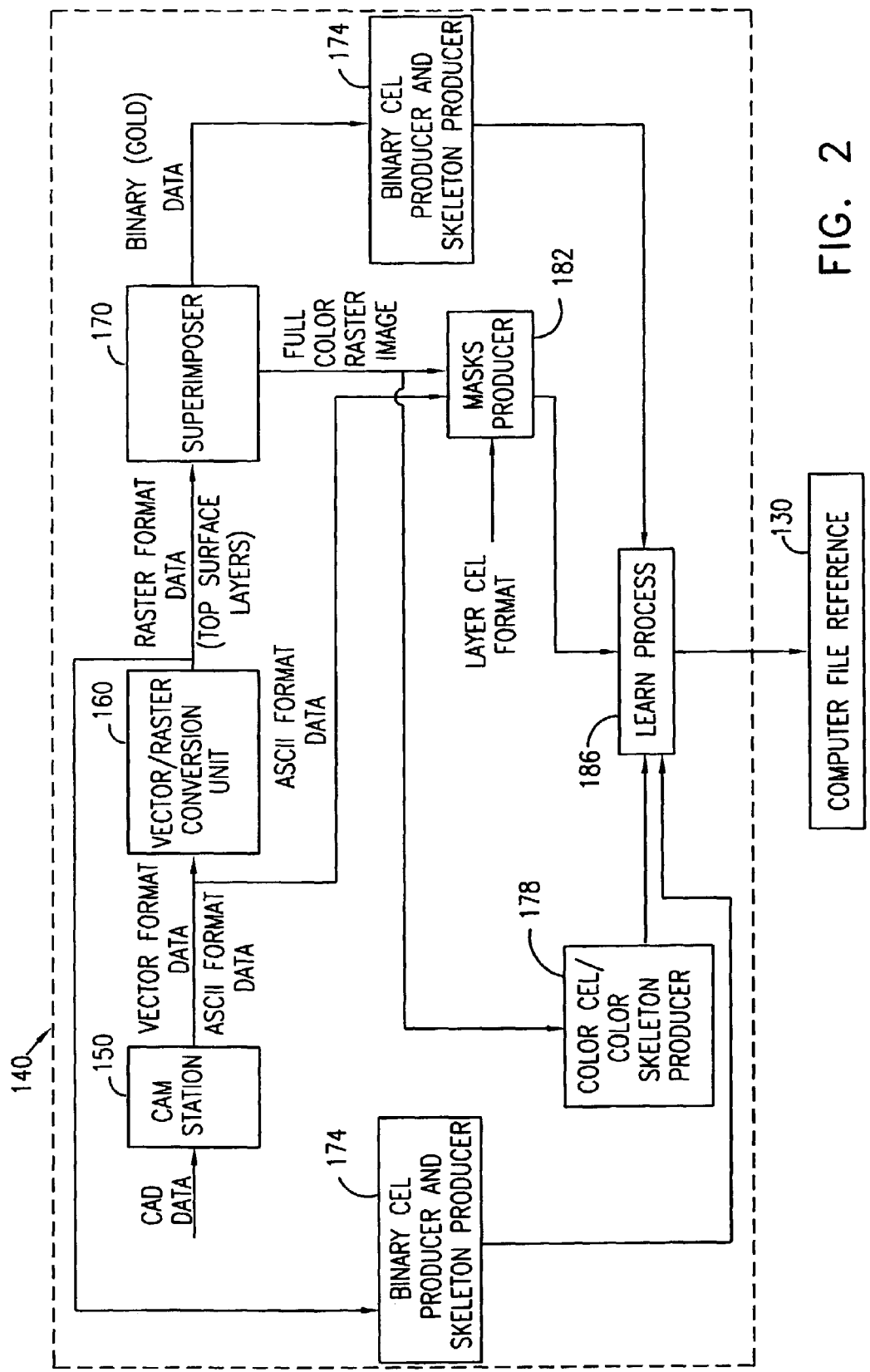
FIG. 2 is a simplified block diagram of a preferred implementation of a portion of the system of FIG. 1 illustrating construction of a computer file reference.

Reference is now made to FIG. 2, which is a simplified block diagram of a preferred implementation of a portion of the system of FIG. 1A illustrating the preparation of a computer file reference. The apparatus of FIG. 2 comprises a preferred implementation of the computer file reference constructor 140 of FIG. 1A. It is appreciated that other preferred implementations are possible, and that the implementation of FIG. 2 is by way of example only, and is not meant to be limiting.

The components of the computer file reference constructor 140 are typically implemented in a combination of hardware and software, as is well known in the art.

The apparatus of FIG. 2 preferably comprises a CAM workstation 150. CAM workstation 150 may comprise any suitable computer workstation, preferably running a commercially available CAM software package for electrical circuit manufacture, such as Xpert™ 1700 CAM software commercially available from Orbotech Ltd. The CAM workstation 150 typically is operative, as is well known in the art, to receive as input CAD data and to produce therefrom CAM data, typically in a vector format used in the operation of electrical circuit manufacturing equipment.

The input CAD data may be in any appropriate format such as, for example, in Gerber format, which is well known in the art of PCB manufacturing for use with computer aided manufacturing files used in imaging systems. The vector format CAM data may be in any appropriate format, such as aoiimg or opf format, which formats are CAM formats widely used in PCB manufacturing. In the present invention, the CAM data (or the CAD data, whichever is used) preferably comprises data defining a plurality of overlays which together form a layer of an electrical circuit, such as the top or outer layer of a BGA. For example, and without limiting the generality of the foregoing, the CAM data may comprise computer files 144, 146, and 148 of FIG. 1A.

The apparatus of FIG. 2 also preferably comprises a vector/raster conversion unit 160. The vector/raster conversion unit 160 may comprise any appropriate unit operative to receive a vector format input and produce a raster format output which forms an image having a plurality of pixel locations and preferably specifies a state for each pixel, such as a binary state designating that each pixel is black or white. Alternatively, a non binary state may be specified. Vector to raster conversion is well known in the art.

It is appreciated that the actual resolution at which image analysis is performed by the inspection subsystem 100 (FIG. 1A) preferably is finer than the optical resolution at which it acquires images of an article being inspected. Accordingly, it is necessary to construct the computer file reference 130 to the level of higher resolution at which image analysis is to be performed by image inspection subsystem 100.

It is appreciated that, alternatively to the CAM station 150, the vector/raster conversion unit 160, and the superimposer 170 described below, other apparatus and/or other means may be used to directly generate raster format data for each of the layers or overlays. For example, the raster format data may be produced directly such as, for example, in a CAM process (not shown), and then supplied to the other components of FIG. 2.

Preferably, the output of the vector/raster conversion unit 160 is received by a binary CEL producer and skeleton producer 174, as well as by the superimposer 170 as described below. The binary CEL producer and skeleton producer 174 preferably is operative to produce binary CELs and skeleton information from the received input. A binary CEL preferably is a CEL defining an edge between any two different homogeneous color populations in an image. A homogeneous color population is a region having a distinctly identifiable optical attribute such as a reflectivity or a color and generally may be correlated to a material or combination of materials. A skeleton is a morphological skeleton of region, produced for example by erosion dilation techniques.

Methods for producing binary CELs and skeleton information from pixels in images are described in co-pending Israel Patent Application 131092, filed Jul. 25, 1999, which has been incorporated herein by reference. Another preferred method for producing binary CELs from raster format information is described in more detail below with reference to FIG. 7.

The apparatus of FIG. 2 also comprises a superimposer 170. The superimposer 170 preferably is operative to superimpose raster format data received from several sources. The data is received from the vector/raster conversion unit 160. Preferably each source, such as a computer file overlay 144, 146 and 148 (FIG. 1A) represents one of various separate deposits or overlays of materials that together with additional information, such as ASCII information describing the location of drilled holes, masked areas not to be inspected and the like (not shown), describe a single layer or inspectable surface of an article to be inspected, such as the top or outer layer of a finished BGA. Thus, for example, as described in greater detail hereinbelow with reference to FIGS. 5A–5D, one source describes regions of copper conductors, one source describes regions of gold plating on copper conductors, and one source describes regions of a solder mask overlay. Preferably, the deposits or overlays are superimposed in mutual registration.

Further preferably, the superimposer 170 is operative to produce an output comprising at least a polychromatic image, also termed herein a color image or a full color raster image, of the electrical circuit. In the polychromatic image, each pixel in the raster is assigned one of a preselected number of colors as a function of which layer, or combination of layers, provides data at the given pixel. The polychromatic image preferably is received by a masks producer 182, which also preferably receives ASCII format data output by the CAM station 150 and CEL format information of one or more layers or overlays, and preferably is operative to produce a mask therefrom defining regions not be inspected.

The superimposer 170, in producing the output thereof, such as a color raster image, preferably takes into account predefined rules governing the result of superimposing various overlays in different ways, and assigns a uniquely identifiable color population to each combination of materials represented by the overlays. The rules preferably incorporate information about the relationship between overlays. For example, if overlays are inputs defining regions of copper conductor, solder mask and gold coatings on conductors respectively, the following rules might be comprised in the predefined rules for determining a color population to be assigned to a pixel:

Conductor+no solder mask+no gold coating=copper

No conductor+no solder mask+no gold coating=bare substrate

Conductor+solder mask+no gold coating=solder mask over copper

Conductor+solder mask+gold coating=solder mask over gold

No Conductor+solder mask+no gold coating=solder mask over substrate

The polychromatic image is also preferably received by a color CEL/color skeleton producer 178, whose operation preferably is similar to that of the binary CEL producer and skeleton producer 174 and is described in more detail below with reference to FIG. 10.

The superimposer 170 is also operative to produce binary data such as binary CEL data, that is, two-value data defining a contour or an edge between any two different homogeneous color populations, representing a "golden" or perfect example, of an image to be inspected. The binary golden data preferably is received by a binary CEL producer and skeleton producer 174, whose operation preferably is as described above.

Preferably, the outputs of binary CEL producer and skeleton producers 174, the color CEL/color skeleton producer 178, and the masks producer 182 emulate a representation of an article being inspected as generated by optical inspection subsystem 100. These outputs are input into a learn process 186 which preferably is operative to produce therefrom the computer file reference 130 which includes, for example, a suitable vectorized representation of collections of CELs or other suitable representation of features in the electrical circuit that are usable as a reference in an inspection system. A preferred implementation of the learn process 186 is described in detail in co-pending Israel Patent Application 131282, filed Aug. 5, 1999, which has been incorporated herein by reference.

Reference is now made to FIG. 3, which is a simplified flow chart illustrating a preferred method of operation of the system of FIG. 1A. The method of FIG. 3 preferably comprises the following steps:

A computer file reference is constructed from computer files representing layers of electrical circuit design (step 190) and preferably is stored offline in a memory. An electric circuit is analyzed using optical inspection (step 200) and an online inspection output is generated. As described above with reference to FIG. 1A, preferably an output of step 200 and the computer file reference produced by step 190 preferably have compatible formats.

The results of the optical inspection are analyzed, typically including comparison with the computer file reference such as by matching corresponding binary CELs and color CELs in electrical circuits being inspected to binary CELs and color CELs in computer file reference (step 210). Analysis and comparison typically takes place online concurrent to optical inspection. An inspection result 215 preferably is produced, typically indicating one or more flaws, if present, in the output of step 190 as compared to the output of step 200.

Reference is now made to FIG. 4, which is a simplified flow chart illustrating operation of part of the system of FIG. 1A, shown in FIG. 2, which relates to generation of a computer file reference. The method of FIG. 4 preferably includes the following steps:

CAD data representing overlays that together form a layer of an electrical circuit is received (step 220) and converted to CAM data, typically to CAM data in a vector format (step 230). The vector format CAM data for each overlay is converted to raster format (step 240). Steps 220, 230, and 240 may be omitted if raster format data for each overlay is supplied initially.

Data representing each of the overlays in the raster format data is mutually superimposed, to produce a representation of a layer of an electrical circuit to be inspected (step 250), preferably comprising a color raster image in which the various homogeneous color populations resulting from combination of overlays are represented. The homogeneous color populations preferably are assigned according to predetermined rules as described hereinabove with reference to superimposer 170 in FIG. 2. Data, including the output of step 250 as well as the output of step 230, is analyzed to produce CELs and skeleton information, preferably both in binary and in color forms, as well as mask information (step 260). The results of step 260, preferably including one or more of binary CELs, skeletons, color CELs and color skeletons, preferably are utilized in a learn process (step 270), to produce a computer file reference representing an ideal electrical circuit to be inspected.

Figure 5A:
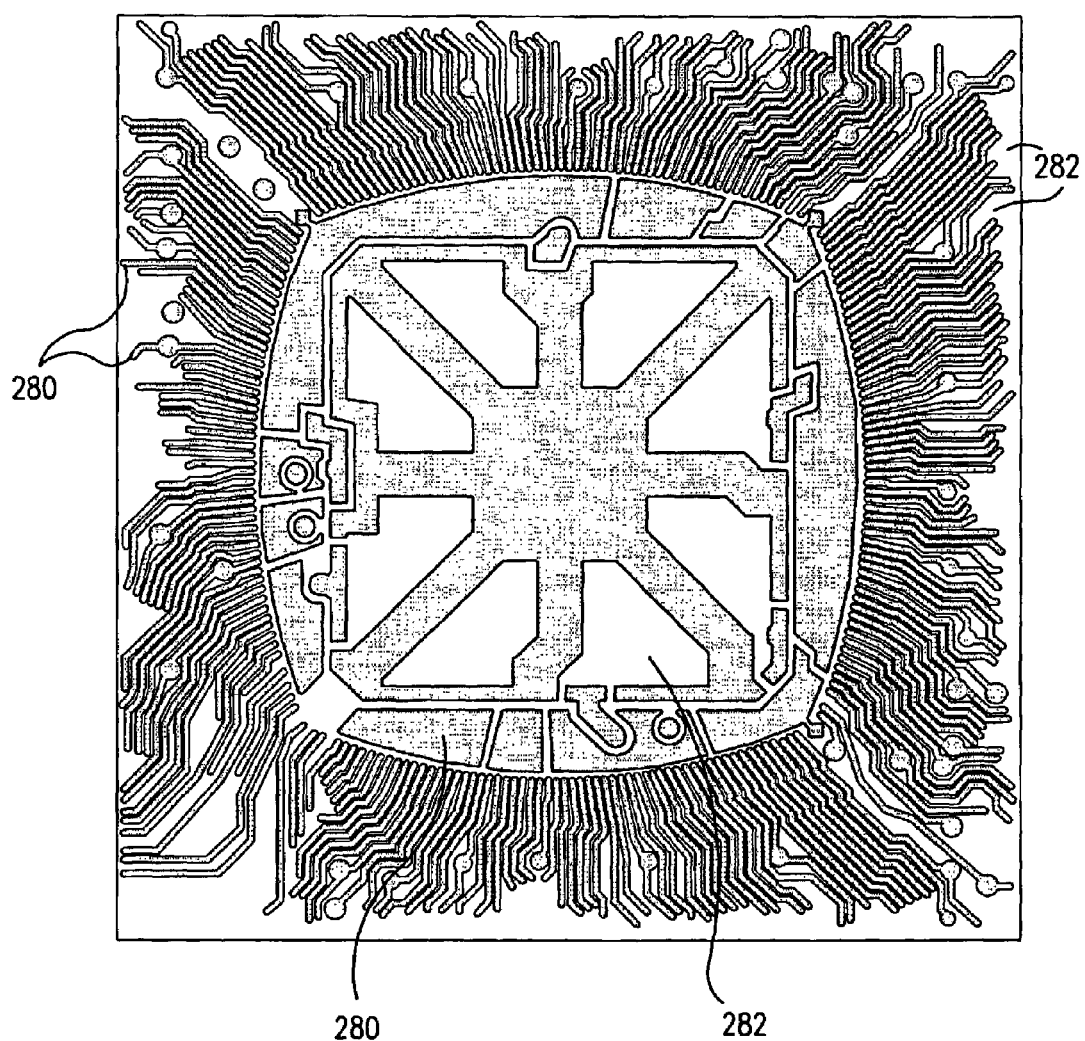
FIGS. 5A–5C are simplified pictorial illustrations of examples of overlays, which may be combined together to comprise an inspectable surface of an electrical circuit.
Figure 5B:
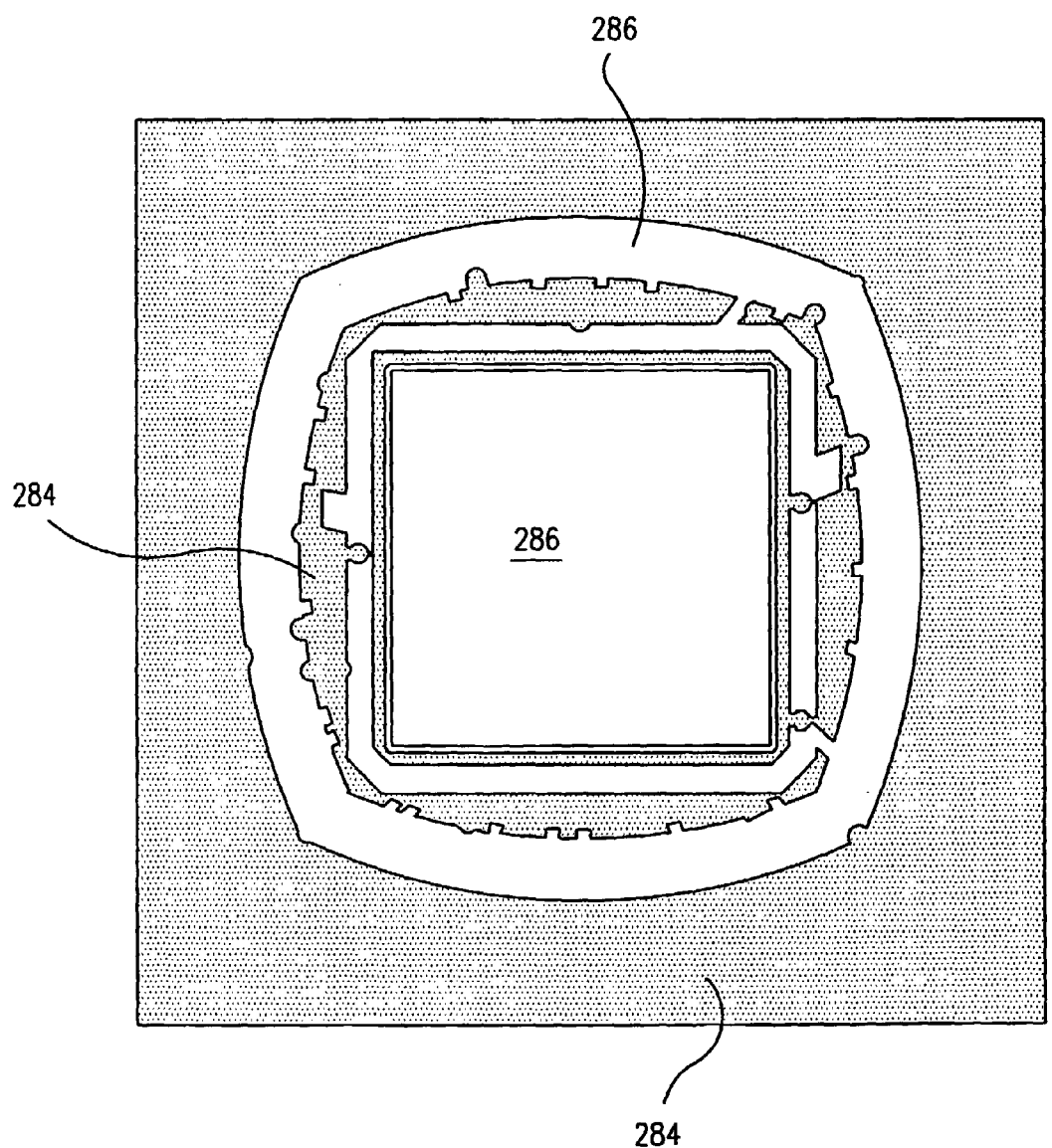
Figure 5C:
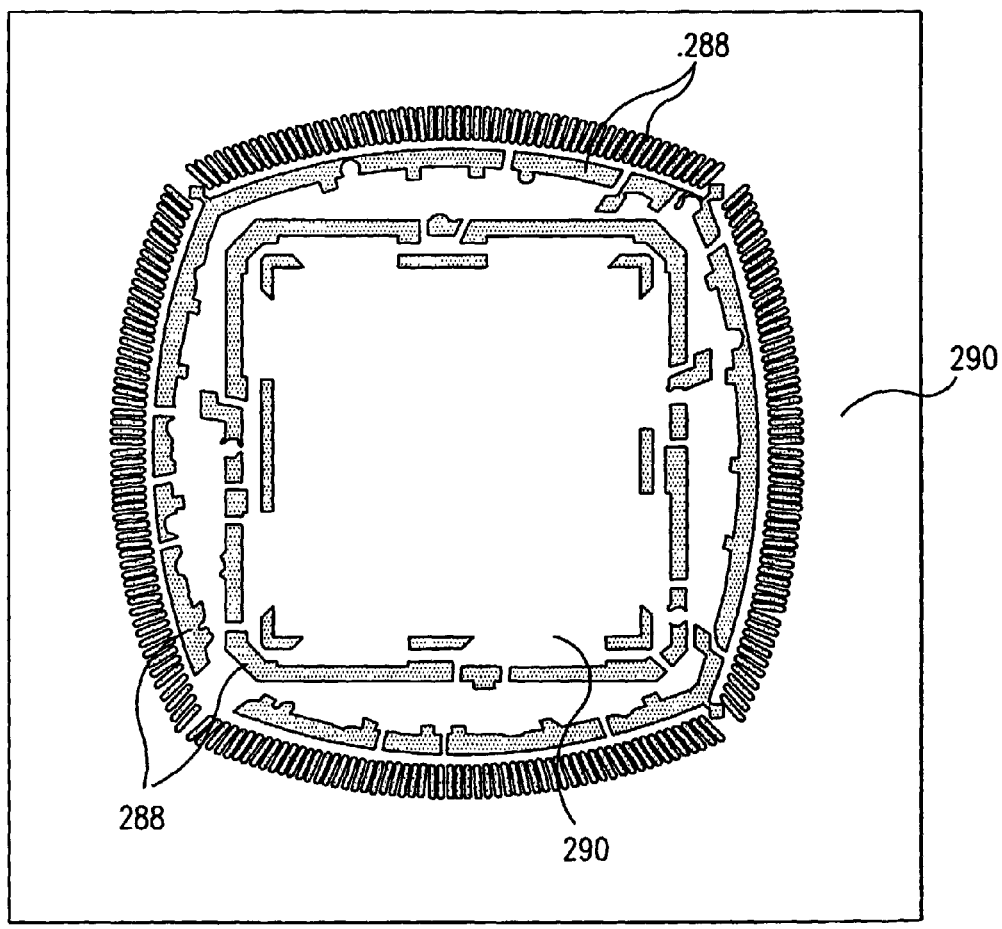

Reference is now made to FIGS. 5A–5D and FIG. 6, which may aid in understanding of the present invention:

FIGS. 5A–5C are simplified pictorial illustrations of examples of overlays, which may be combined together to comprise a representation of an inspectable surface of an electrical circuit such as a BGA. In the example shown, FIG. 5A is a simplified pictorial illustration of an overlay indicating regions of copper conductor 280 and regions of substrate 282. FIG. 5B is a simplified pictorial illustration of an overlay indicating regions covered by translucent solder mask 284, and regions not covered by translucent solder mask 286. FIG. 5C is a simplified pictorial illustration of an overlay indicating regions of gold plating 288 and regions that are not gold plated 290.

Figure 5D:
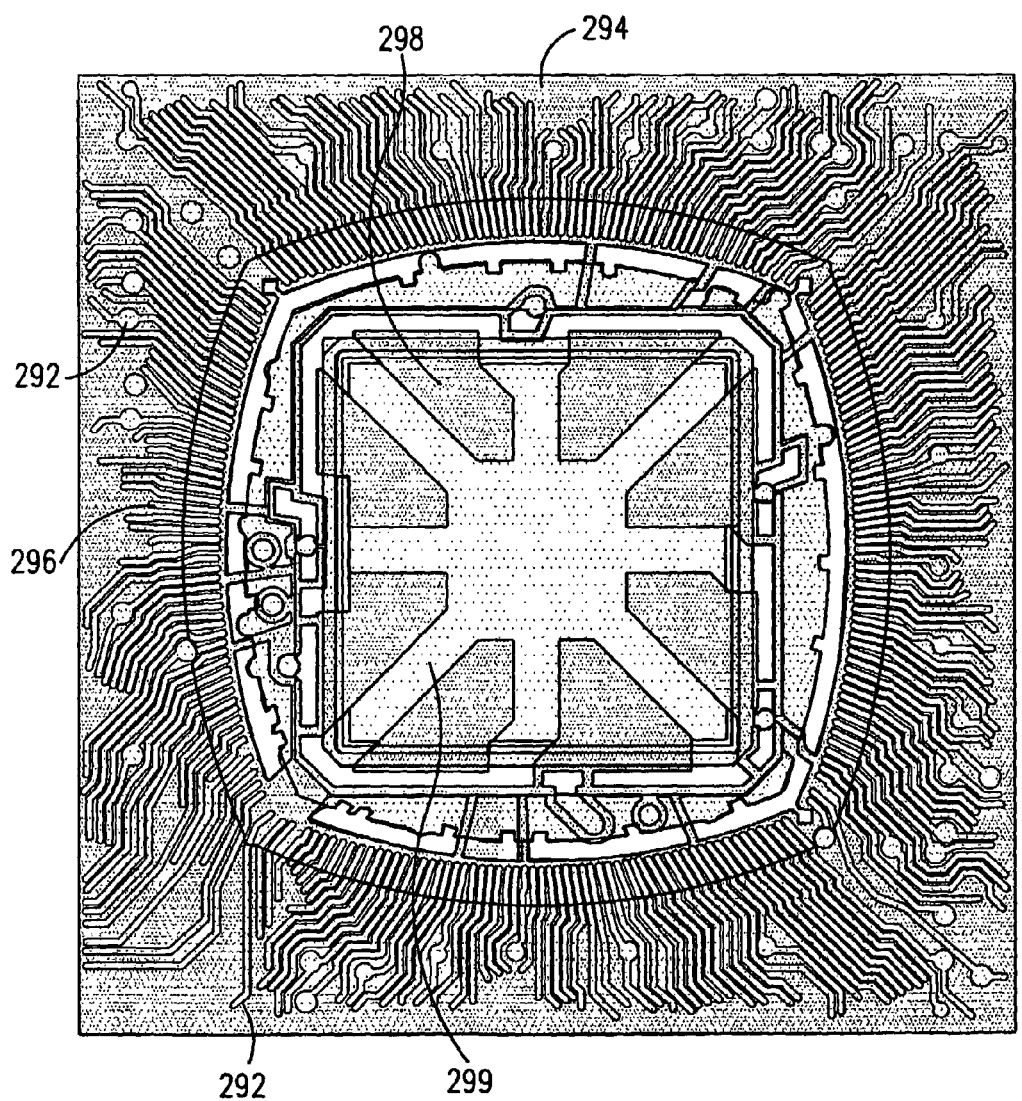
FIG. 5D is a simplified pictorial illustration of an example of an inspectable surface of an electrical circuit, which may be comprised of the overlays of FIGS. 5A–5C.

FIG. 5D is a simplified pictorial illustration of an example of an inspectable surface of an electrical circuit, for example an outer layer of a BGA, which may be comprised of the overlays of FIGS. 5A–5C, in which the following are shown: regions of copper conductor covered by solder mask 292, regions of substrate covered by solder mask 294, regions of copper conductor coated by gold 296 and regions of bare substrate 298, regions of bare copper 299.

Figure 6:
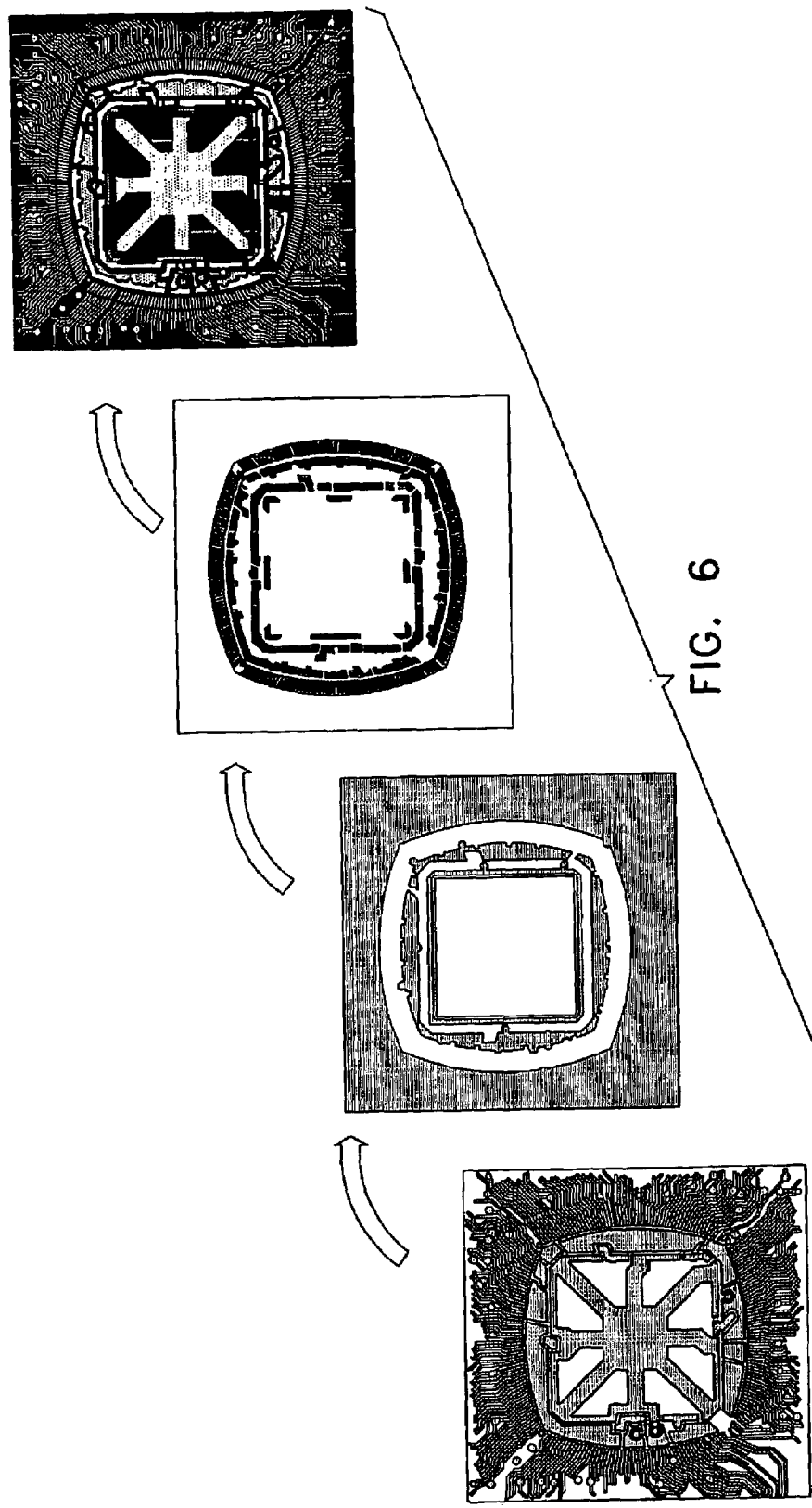
FIG. 6 is a simplified pictorial illustration of the combination of the overlays of FIGS. 5A–5C to comprise the inspectable surface of FIG. 5D.

FIG. 6 is a simplified pictorial illustration of the process of combining of the overlays of FIGS. 5A–5C to comprise a representation of the inspectable surface of FIG. 5D.

FIGS. 5A–5D and 6 generally are self-explanatory with reference to the above description, particularly the description of FIG. 2.

Figure 7:
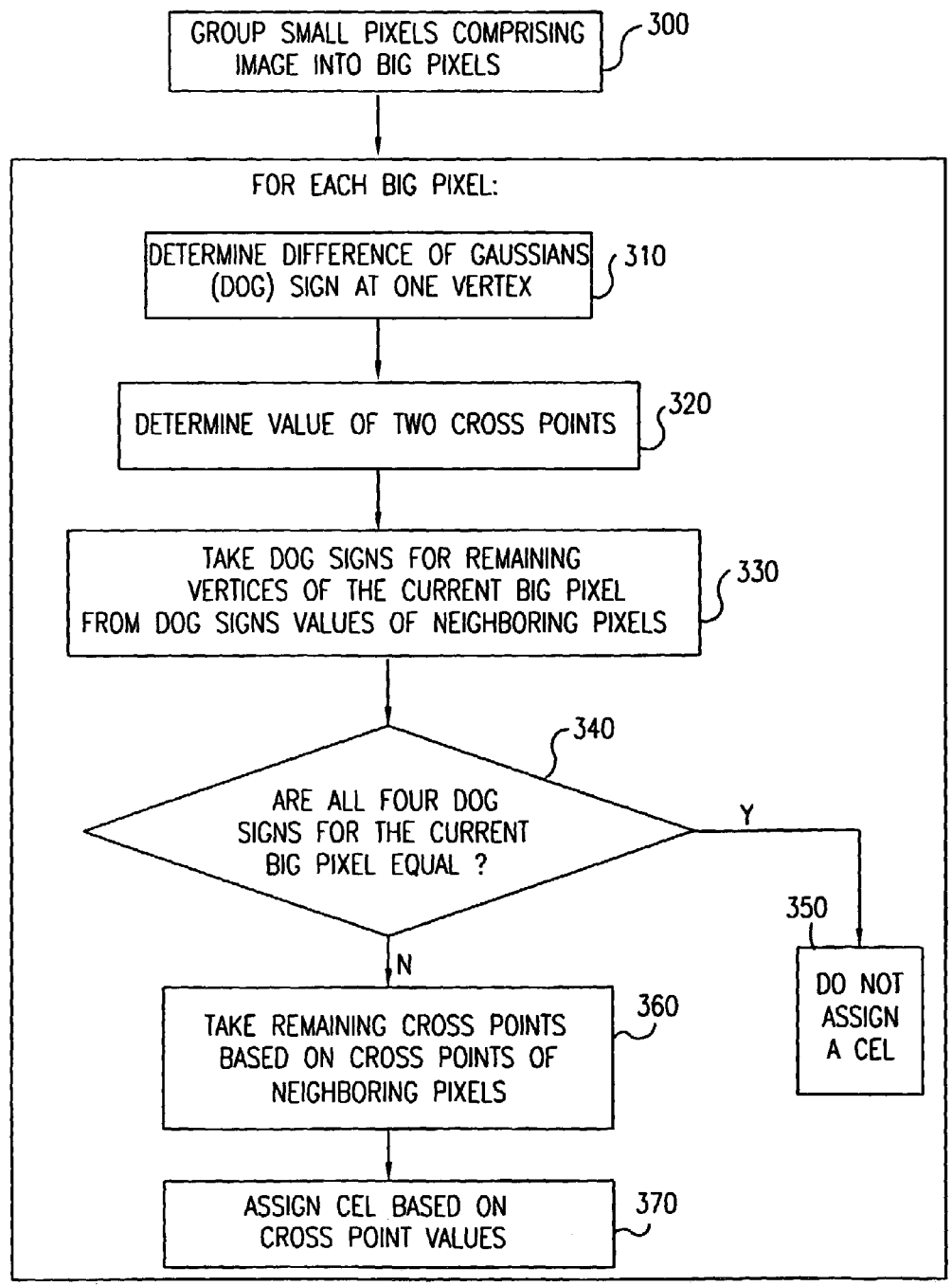
FIG. 7 is a simplified flowchart illustration of a preferred method of operation of a portion of the apparatus of FIG. 2, which relates to binary CEL generation.

Reference is now made to FIG. 7, which is a simplified flowchart illustration of a preferred method of operation of the binary CEL producer and skeleton producer 174 of FIG. 2. The method of FIG. 7 comprises a preferred implementation of CEL production from CAM data input which may be performed on a single overlay as shown in any of FIGS. 5A, 5B or 5C, or on a superimposed image such as is shown in FIG. 5D, so as to produce CELs for boundaries between various combinations of materials in the electrical circuit layer as may be desired to produce a computer file reference 130. Methods described in co-pending Israel Patent Application 131092, filed Jul. 25, 1999, which has been incorporated herein by reference, may be used for skeleton production from raster data input.

The method of FIG. 7 preferably comprises the following steps:

Small pixels comprising the input raster image are grouped into big pixels (step 300) wherein each big pixel preferably corresponds in size to an optical pixel in an optical inspection subsystem 100 (FIG. 1A). Each big pixel preferably comprises a rectangular array of small pixels. The small pixels preferably correspond in size to the subpixel resolution at which optical inspection subsystem 100 operates during online inspection and image processing of electrical circuits. Typically, the sub-pixel resolution image generation of an image of object, such as an electrical circuit being inspected, is performed generally as described in U.S. Pat. Nos. 5,774,572 and 5,774,573 to Caspi et al.

Figure 8:
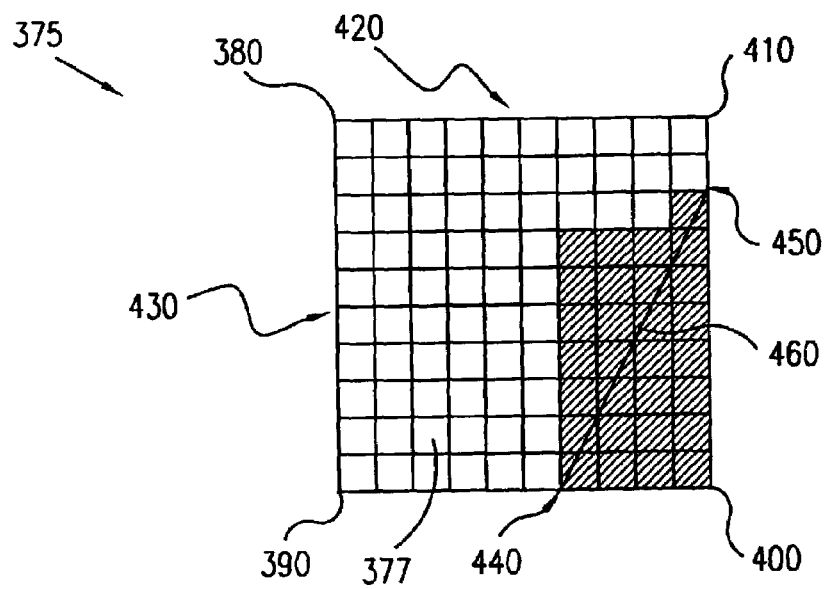
FIG. 8 is a simplified pictorial illustration of a big pixel, comprising a plurality of small pixels, useful in understanding the method of FIG. 7.

Reference is now additionally made to FIG. 8, which is a simplified pictorial illustration of a big pixel, comprising a plurality of small pixels, useful in understanding the method of FIG. 7. In FIG. 8 a single big pixel 375 is illustrated. Big pixel 375 comprises a plurality of small pixels 377, arranged in a rectangular array. The big pixel 375 preferably comprises an array of 4×4 or 16×16 small pixels; an array size of 10×10 is shown for purposes of simplicity of illustration only and is not meant to be limiting. Generally, the array size will correspond to the array size used by the vector/raster conversion unit 160 (FIG. 2), as described above with reference to FIG. 2, which preferably corresponds to a sub-optical pixel definition employed in the optical inspection subsystem 100.

The remaining steps of FIG. 7 preferably are performed once for each big pixel, preferably in accordance with a pre-defined scan pattern, as is well-known in the art.

A difference of Gaussians (DOG) sign is determined at one vertex of each big pixel 375 (step 310). The DOG sign is the positive/negative sign of the second derivative of the intensity of an optical pixel at the current point in a function of optical pixel intensities, and preferably is chosen so that, if the optical intensity of the current big pixel is relatively dark the sign is positive, and otherwise it is negative. DOG signs are indicative of an edge of an optical pixel through which an edge in the pattern on an article being inspected passes. Thus an edge passes between vertices of an optical pixel 375 that have oppositely signed positive/negative DOG signs while no edge passes between vertices having the same DOG sign.

The DOG sign may be determined at any of the four vertices 380, 390, 400, and 410 as shown in FIG. 8. However, as will be described below, for the sake of connectivity of CELs between adjoining big pixels, the DOG point of only a single vertices is determined for each big pixel 375, and the DOG signs for other vertices are taken from neighboring big pixels.

The DOG signs determined at the four vertices are referred to herein respectively as DOG sign 0, DOG sign 1, DOG sign 2, and DOG sign 3 which correspond to vertices 380, 390, 400 and 410 respectively. For the sake of simplicity of description, the description of the steps of FIG. 7 assumes that DOG sign 2 located at vertex 400 is used, but it is appreciated that a skilled person of the art would be able to choose a different DOG sign and would vary the remainder of the method of FIG. 7 accordingly.

Methods of computing a DOGs in pixel images acquired during the inspection of an electrical circuit are well known in the art, and are described, for example, in co-pending Israel Patent Application 131092, filed Jul. 25, 1999, which has been incorporated herein by reference. Methods for computing a DOG are also described in the following United States Patents, which have been incorporated herein by reference: U.S. Pat. No. 5,774,572 to Caspi; and U.S. Pat. No. 5,774,573 to Caspi et al. It is appreciated by persons skilled in the art that the DOG sign may be computed alternatively, in a raster image, simply based on the relationship between two color populations contained in a big pixel. If one of the populations is lighter than the other than preferably, the DOG sign of the lighter population is negative and the DOG sign of the darker population is positive. Determination of the DOG value preferably is made by counting the number of dark small pixels in the current big pixel, relative to its neighbors. In this manner, a complete DOG computation, as described in the references cited above, is not necessary.

The values of two cross points are determined by the number of small pixels at the edge for the current big pixel (step 320). The value of a cross point refers to a value allocated for an edge 420, 430, 444 or 450 of a big pixel 375 as a function of the point along the edge 420, 430, 444 and 450 of a big pixel at which a transition occurs between light and dark small pixels. The existence of a transition is indicated by oppositely signed DOG signs at neighboring vertices.

It is appreciated that a cross point may be determined simply by identifying where the small pixels along an edge change from a binary 0 to binary 1, or vice versa. In FIG. 8, valued cross points, namely cross points for which a change in value occurs, are shown associated with edge 440 and edge 450. It is noted that there is no transition of small pixels from light to dark (binary 0 to binary 1), along either of edges 420 or 430. For tracking purposes, edges 420 and 430 preferably are assigned a cross point value, such as −1, indicating that no transition of small pixels occurs along that edge. Each of the edges 440 and 450 may be assigned a cross point value, indicating which small pixel along the corresponding edge the transition is found to occur. A preferred data structure for representing CELs is described in Israel Patent Application 131282, which has been incorporated herein by reference.

Preferably, for each big pixel, as will be described below, cross point values are determined for two edges only in a big pixel, wherein the cross point value for each of the other edges in a big pixel are taken from neighboring big pixels. For the sake of simplicity of description, it is assumed that cross point values are determined for edge 440 and edge 450 in step 320, but it is appreciated that persons skilled in the art could choose another two edges, and the remainder of the method of FIG. 7 would vary accordingly.

Preferably, if more than one transition from light to dark, or vice versa, in small pixels is found on a given edge only one transition such as, for example, the first transition, is used for that edge. The first transition may be determined arbitrarily, for example along a horizontal pixel edge as being the left most transition, and along a vertical pixel edge as being the top most transition, or vise versa. It is appreciated that, if the first transition is used, searching for an additional transition on the edge preferably ceases. Additionally, continuity between adjoining big pixels of cross point values is maintained by taking cross point values for two edges from neighboring big pixels, in step 360 discussed below, as needed Inasmuch as a DOG sign is computed for a single vertex of a big pixel, DOG signs are determined for the three remaining vertices of the current big pixel by taking the DOG values at vertices of neighboring pixels (step 330), it being appreciated that the DOG values at neighboring big pixels are determined and buffered before step 330 is carried out.

Figure 9:
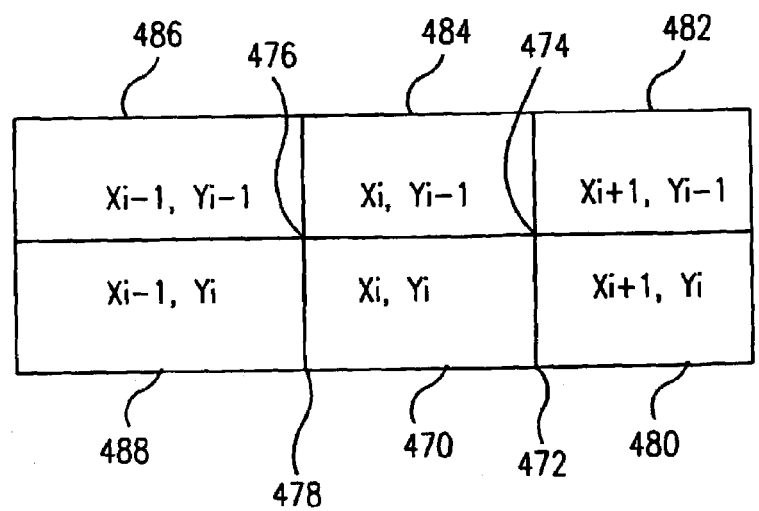
FIG. 9 is a simplified pictorial illustration of a big pixel and its neighbors, useful in understanding the method of FIG. 7.

Reference is now additionally made to FIG. 9, which is a simplified pictorial illustration of a big pixel and its neighbors, useful in understanding the method of FIG. 7. In FIG. 9 a current big pixel 470, designated pixel Xi,Yi and having vertices 472, 474, 476 and 478, and five neighboring pixels, designated pixels Xi+1,Yi 480, Xi+1,Yi−1 482, Xi,Yi−1 484, Xi−1,Yi−1 486, and Xi−1,Yi 488 are shown. It will be appreciated by persons skilled in the art that if the DOG value at vertex 472 is determined for pixel 470, then the 3 remaining DOG signs for vertices 474, 476 and 478 (corresponding to vertices 380, 390, and 410 in FIG. 8) are logically determined by, and therefore may be determined based on, DOG signs of the neighboring pixels. Thus, for example the DOG signs of vertex 474 may be taken from pixel 484, the DOG signs of vertex 476 may be taken from pixel 486 and the DOG signs of vertex 478 may be taken from pixel 488.

A check is made as to whether all four DOG signs for the current big pixel are equally signed (step 340). If all four DOG signs are equally signed (positive/negative), thereby indicating that no transition from white to black occurs in the current big pixel, then no edge passes through current big pixel 375, and no CEL is assigned to the current big pixel 375 (step 350). If not all four DOG signs are equally signed, then the cross point values for the remaining edges are taken based on the corresponding cross point values found in neighboring big pixels. The determination of values for remaining cross points from neighbors is self-explanatory with reference to the above discussion of step 330 and FIGS. 8 and 9.

If not all DOG signs are equal (positive/negative), then a CEL is assigned based on the cross point values as previously determined (step 370). The end points of the CEL are based on cross point values, and a vectorized direction preferably is assigned to a CEL is based on the orientation of the white and black regions in big pixel 375 relative to the CEL. Referring again to FIG. 8, CEL 460 is based on cross points along edges 440 and 450. A preferred data structure for a CEL including its vector direction, is described in Israel Patent Application 131282 which has been incorporated herein by reference.

Reference is now made to FIG. 10, which is a simplified flowchart illustration of a preferred method of operation of the color CEL/color skeleton producer 178 of FIG. 2. Except as otherwise stated, the method of FIG. 10 is similar to the method of FIG. 7 and is to be understood with reference to the above discussion of FIG. 7. It is appreciated that the input to FIG. 10 preferably comprises a color raster image in which each pixel of the raster is assigned a color, preferably one of a predetermined number of colors corresponding to a homogeneous color population that is associated with a combination of overlays of materials on the surface of an article to be inspected. The assignment of a color is preferably performed by operation of rules as described above with reference to superimposer 170 (FIG. 2).

The method of FIG. 10 preferably comprises the following steps:

After performing step 300, as described above with reference to FIG. 7, the number of different colors represented by the small pixels making up the current big pixel is determined and a decision is made based on the number of colors present in the big pixel (step 490):

1. If the number of colors in the current big pixel is 1, no edge exists in the current big pixel and no CEL is assigned to the current big pixel (step 350).

2. If the number of colors in the current big pixel is greater than 2, a junction is assigned to the current big pixel (step 500). Junctions are described in co-pending Israel Patent Application 131092, filed Jul. 25, 1999, which has been incorporated herein by reference.

3. If the number of colors in the current big pixel is equal to 2, the method preferably continues at step 1310 in a similar manner as in the method of FIG. 7, (step 310). It is appreciated that, in this case, a color DOG or CDOG, is determined. In the CDOG both color and relative pixel intensity are considered. The CEL assigned in step 1370 preferably comprises a color CEL including information on the two colors in the current big pixel, typically as described in co-pending Israel Patent Application 131092, filed Jul. 25, 1999, referred to above.

It is appreciated that because the assignment of a sign to a CDOG takes into account the color, it is necessary to apply consistent logic in determining whether such a sign is positive or negative. Thus in accordance with a preferred embodiment of the invention, the sign, positive or negative, is determined as a function of a color, preferably according to the following hierarchy:

1. gold
2. copper
3. solder mask over metal
4. solder mask over substrate
5. bare substrate When a big pixel includes colors representative of any of the two of the above materials, the material that is higher in the hierarchy preferably is assigned a negative CDOG value, while the material lower in the hierarchy is assigned a positive CDOG value. For example, if a big pixel includes small pixels representative of gold and solder mask over substrate, the vertices of the big pixel are assigned a negative CDOG value where the small pixels of gold are located, while the vertices of the big pixel are assigned a positive CDOG value where small pixels of solder mask over substrate are located.

It is appreciated that steps 1310, 1320, and 1360 are similar to steps 310, 320, and 360 of FIG. 7 respectively; steps 1330, 1340, and 1370 correspond to steps 330, 340, and 370, respectively, of FIG. 7, with the use of CDOG in place of DOG.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited by what has been particularly shown and described hereinabove. Rather the scope of the invention is defined only by the claims which follow:

What is claimed is:

1. An electrical circuit inspection system comprising:
   an optical subsystem for optically inspecting an electrical circuit and providing an inspection output identifying more than two different types of regions; and
   an analysis subsystem for analyzing said inspection output, said analyzing including comparing said inspection output with a computer file reference identifying more than two different types of regions that are distinguishable at least by an optical characteristic;

wherein said more than two different types of regions include an exposed first metal region, a first metal region covered by a translucent material, an exposed second metal region, a second metal region covered by a translucent material, an exposed substrate and a substrate covered by said translucent material.

2. An electrical circuit inspection system according to claim 1 and wherein said optical subsystem is capable of optically inspecting more than one layer of an electrical circuit and said more than two different types of regions include regions at more than one layer of said electrical circuit.

3. An electrical circuit inspection system according to claim 1 and wherein said more than two different types of regions include an exposed metal region, a metal region covered by a translucent material, an exposed substrate and a substrate covered by said translucent material.

4. An electrical circuit inspection system according to claim 3 and wherein said translucent material is a solder mask.

5. An electrical circuit inspection system according to claim 3 and wherein said translucent material is a polyamide layer.

6. An electrical circuit inspection system according to claim 1 and wherein said translucent material is a solder mask.

7. An electrical circuit inspection system according to claim 1 and wherein said translucent material is a polyamide layer.

8. An electrical circuit inspection system according to claim 1 and wherein said computer file reference identifying more than two different types of regions comprises a composite of multiple computer files, each representing a different layer of said electrical circuit.

9. An electrical circuit inspection system according to claim 1 and wherein said computer file reference identifying more than two different types of regions comprises an overlay of multiple computer files, each representing a different layer of said electrical circuit.

10. An electrical circuit inspection system according to claim 1 and wherein said computer file reference identifying more than two different types of regions comprises multiple computer files, each representing a different layer of said electrical circuit, superimposed in mutual registration.

11. An electrical circuit inspection system according to claim 1 and wherein said computer file reference comprises a computer file of at least one metal layer and at least one layer of a translucent material overlying said at least one metal layer, superimposed in mutual registration.

12. An electrical circuit inspection system according to claim 1 and wherein said computer file reference is a polychromatic reference.

13. An electrical circuit inspection system according to claim 1 and wherein said inspection output is a polychromatic output.

14. An electrical circuit inspection system according to claim 1 and wherein said computer file reference comprises at least one CAM file.

15. Apparatus for constructing a computer file reference identifying more than two different types of regions on an electrical circuit, comprising: a superimposer for superimposing in mutual registration at least two computer files, each computer file representing a different portion of said electrical circuit, wherein said more than two different types of regions include an exposed first metal region, a first metal region covered by a translucent material, an exposed second metal region, a second metal region covered by a translucent material, an exposed substrate and a substrate covered by said translucent material.

16. Apparatus according to claim 15 and wherein the different types of regions are optically distinguishable.

17. Apparatus according to claim 5 and wherein the portion is a layer of the electrical circuit, and a plurality of layers form an inspectable surface of the electrical circuit.

18. Apparatus according to claim 15 and wherein said more than two different types of regions include an exposed metal region, a metal region covered by a translucent material, an exposed substrate and a substrate covered by said translucent material.

19. Apparatus according to claim 18 and wherein said translucent material is a solder mask.

20. Apparatus according to claim 18 and wherein said translucent material is a polyamide layer.

21. Apparatus according to claim 15 and wherein said translucent material is a solder mask.

22. Apparatus according to claim 15 and wherein said translucent material is a polyamide layer.

23. Apparatus according to claim 15 and wherein said computer file reference identifying more than two different types of regions comprises a composite of multiple computer files, each representing a different layer of said electrical circuit.

24. Apparatus according to claim 15 and wherein said computer file reference identifying more than two different types of regions comprises an overlay of multiple computer files, each representing a different layer of said electrical circuit.

25. Apparatus according to claim 15 and wherein said computer file reference identifying more than two different types of regions comprises multiple computer files, each representing a different layer of said electrical circuit, superimposed in mutual registration.

26. Apparatus according to claim 15 and wherein said computer file reference comprises a computer file of at least one metal layer and at least one layer of a translucent material overlying said at least one metal layer, superimposed in mutual registration.

27. Apparatus according to claim 15 and wherein said computer file reference comprises at least one CAM file.

28. An electrical circuit inspection system comprising:
an optical subsystem for optically inspecting an electrical circuit and providing an inspection output identifying edges between at least two different regions in the electrical circuit; and
an analysis subsystem for analyzing said inspection output, said analyzing including comparing said inspection output with a computer file reference formed from at least one CAM file corresponding to said electrical circuit and identifying edges between at least two different regions;
wherein said at least two different regions include an exposed first metal region, a first metal region covered by a translucent material, an exposed second metal region, a second metal region covered by a translucent material, an exposed substrate and a substrate covered by said translucent material.

29. An electrical circuit inspection system according to claim 28 and wherein said optical subsystem is capable of optically inspecting more than one layer of an electrical circuit and said at least two different regions include regions at more than one layer of said electrical circuit.

30. An electrical circuit inspection system according to claim 28 and wherein said at least two different regions include an exposed metal region, a metal region covered by a translucent material, an exposed substrate and a substrate covered by said translucent material.

31. An electrical circuit inspection system according to claim 30 and wherein said translucent material is a solder mask.

32. An electrical circuit inspection system according to claim 30 and wherein said translucent material is a polyamide layer.

33. An electrical circuit inspection system according to claim 28 and wherein said translucent material is a solder mask.

34. An electrical circuit inspection system according to claim 28 and wherein said translucent material is a polyamide layer.

35. An electrical circuit inspection system according to claim 28 and wherein said computer file reference identifying at least two different regions comprises a composite of multiple computer files, each representing a different layer of said electrical circuit.

36. An electrical circuit inspection system according to claim 28 and wherein said computer file reference identifying at least two different regions comprises an overlay of multiple computer files, each representing a different layer of said electrical circuit.

37. An electrical circuit inspection system according to claim 28 and wherein said computer file reference identifying at least two different regions comprises multiple computer files, each representing a different layer of said electrical circuit, superimposed in mutual registration.

38. An electrical circuit inspection system according to claim 28 and wherein said computer file reference comprises a computer file of at least one metal layer and at least one layer of a translucent material overlying said at least one metal layer, superimposed in mutual registration.

39. An electrical circuit inspection system according to claim 28 and wherein said computer file reference is a polychromatic reference.

40. An electrical circuit inspection system according to claim 28 and wherein said inspection output is a polychromatic output.

41. An electrical circuit inspection system according to claim 28 and wherein said computer file reference comprises at least one CAM file.

42. An electrical circuit inspection system according to claim 28 and wherein said computer file reference comprises a plurality of CAM files.

43. A method for electrical circuit inspection comprising:
   optically inspecting an electrical circuit and providing an inspection output identifying edges between at least two different regions in the electrical circuit; and
   analyzing said inspection output, said analyzing including comparing said inspection output with a computer file reference formed from at least one CAM file corresponding to said electrical circuit and identifying edges between at least two different regions;
   wherein said at least two different regions include an exposed first metal region, a first metal region covered by a translucent material, an exposed second metal region, a second metal region covered by a translucent material, an exposed substrate and a substrate covered by said translucent material.

44. A method according to claim 43 and wherein said optically inspecting includes optically inspecting more than one layer of an electrical circuit and said at least two different regions include regions at more than one layer of said electrical circuit.

45. A method according to claim 43 and wherein said at least two different regions include an exposed metal region, a metal region covered by a translucent material, an exposed substrate and a substrate covered by said translucent material.

46. A method according to claim 45 and wherein said translucent material is a solder mask.

47. A method according to claim 45 and wherein said translucent material is a polyamide layer.

48. A method according to claim 43 and wherein said translucent material is a solder mask.

49. A method according to claim 43 and wherein said translucent material is a polyamide layer.

50. A method according to claim 43 and wherein said computer file reference identifying at least two different regions comprises a composite of multiple computer files, each representing a different layer of said electrical circuit.

51. A method according to claim 43 and wherein said computer file reference identifying at least two different regions comprises an overlay of multiple computer files, each representing a different layer of said electrical circuit.

52. A method according to claim 43 and wherein said computer file reference identifying at least two different regions comprises multiple computer files, each representing a different layer of said electrical circuit, superimposed in mutual registration.

53. A method according to claim 43 and wherein said computer file reference comprises a computer file of at least one metal layer and at least one layer of a translucent material overlying said at least one metal layer, superimposed in mutual registration.

54. A method according to claim 43 and wherein said computer file reference is a polychromatic reference.

55. A method according to claim 43 and wherein said inspection output is a polychromatic output.

56. A method according to claim 43 and wherein said computer file reference comprises at least one CAM file.

57. A method according to claim 43 and wherein said computer file reference comprises a plurality of CAM files.

* * * * *